US008563700B2

(12) United States Patent
Lutz et al.

(10) Patent No.: US 8,563,700 B2
(45) Date of Patent: Oct. 22, 2013

(54) SYNERGISTIC EFFECTS

(75) Inventors: Robert J. Lutz, Wayland, MA (US);
Kathleen R. Whiteman, Wilmington, MA (US)

(73) Assignee: ImmunoGen, Inc., Waltham, NH (US)

( * ) Notice: Subject to any disclaimer, the term of this patent is extended or adjusted under 35 U.S.C. 154(b) by 216 days.

(21) Appl. No.: 12/485,446

(22) Filed: Jun. 16, 2009

(65) Prior Publication Data

US 2010/0028346 A1 Feb. 4, 2010

Related U.S. Application Data

(60) Provisional application No. 61/061,886, filed on Jun. 16, 2008.

(51) Int. Cl.
*C07K 16/30* (2006.01)
*C07K 16/28* (2006.01)
*A61K 39/395* (2006.01)

(52) U.S. Cl.
USPC .................. 530/391.7; 424/181.1; 530/388.9; 530/389.8

(58) Field of Classification Search
None
See application file for complete search history.

(56) References Cited

U.S. PATENT DOCUMENTS

| | | | |
|---|---|---|---|
| 5,843,937 A * | 12/1998 | Wang et al. | 514/202 |
| 2004/0265307 A1 | 12/2004 | Singh et al. | |
| 2005/0244413 A1 | 11/2005 | Adolf et al. | |
| 2007/0248604 A1 | 10/2007 | Desnoyers et al. | |

FOREIGN PATENT DOCUMENTS

| | | |
|---|---|---|
| WO | 01/24763 A2 | 4/2001 |
| WO | 2008/019378 A1 | 2/2008 |

OTHER PUBLICATIONS

Rajkumar et al. Combination therapy with lenalidomide plus dexamethasone (Rev/Dex) for newly diagnosed myeloma. Blood, 2005, vol. 106, No. 13, pp. 4050-4053.*
Kumar et al. Thalidomide and lenalidomide in the treatment of multiple myeloma. European Journal of Cancer 2006, vol. 42, pp. 1612-1622.*
Weber et al. Lenalidomide plus dexamethasone for relapsed multiple myeloma in North America. The New England Journal of Medicine, 2007, vol. 357, No. 21, pp. 2133-2142.*
Robert J. Lutz, et al., "Efficacy of the HuN901-DM1 Conjugate in Combination with Antineoplastic Agents against Multiple Myeloma Cells in Preclinical Studies", AACR-2007 Annual Meeting, Apr. 2007 (Los Angeles), Abstract #5577.

(Continued)

*Primary Examiner* — Shafiqul Haq
(74) *Attorney, Agent, or Firm* — Sterne, Kessler, Goldstein & Fox P.L.L.C.

(57) ABSTRACT

The present invention encompasses a combination of at least one conjugate and one or more chemotherapeutic agent(s) which when administered exerts an unexpectedly enhanced therapeutic effect. The therapeutic effectiveness of the combination is greater than that of the conjugate alone or the administration of one or more of the drug(s) without the conjugate. The present invention is also directed to compositions comprising at least one conjugate and at one or more of chemotherapeutic agent and to methods of treating cancer using at least one conjugate and at least one or more of chemotherapeutic agent(s). The present invention also provides methods of modulating the growth of selected cell populations, such as cancer cells, by administering a therapeutically effective amount of one or more chemotherapeutic agent(s) and at least one conjugate. In each case, such combination has therapeutic synergy or improves the therapeutic index in the treatment of cancer over the anticancer agent(s) alone.

45 Claims, 19 Drawing Sheets

Triple combination of huN901-DM1 with lenalidomide plus low-dose dexamethasone in MOLP-8 multiple myeloma xenografts.

(56) References Cited

OTHER PUBLICATIONS

Kathleen R. Whiteman, et al., "Efficacy of IMGN901 (huN901-DM1) in Combination with Bortezomib and Lenalidomide against Multiple Myeloma Cells in Preclinical Studies", AACR-2008 Annual Meeting, Apr. 2008 (San Diego), Abstract #2146.
International Search Report dated Dec. 23, 2009, as issued in International Application No. PCT/US2009/47449.
Ravi V.J. Chari et al., "HuN901-DM1: A tumor-activated prodrug that eradicates large xenografts of small cell lung cancer in mice and shows minimal toxicity in cynomolgus monkeys", AACR, 2000, Abstract 461.
Ravi V.J. Chari et al., "Preclinical Development of huN901-DM1: A Tumor-Activated Prodrug Directed against Small Cell Lung Cancer", AACR, 2000, Abstract 118.
Anthony Tolcher et al., "A Phase I and Pharmacokinetic Study of BB-10901,a Maytansinoid Immunoconjugate, in CD56 Expressing Tumors", EORTC, Nov. 2002.
Pierfrancesco Tassone et al., "In Vitro and in Vivo Activity of the Maytansinoid Immunoconjugate huN901-$N^2$-Deacetyl-$N^2$-(3-Mercapto-1-Oxopropyl)-Maytansine against $CD56^+$Multiple Myeloma Cells", Cancer Res., 2004, 64: 4629-4636.
Lintao Wang et al., "Structural characterization of the maytansinoid—monoclonal antibody immunoconjugate, huN901—DM1, by mass spectrometry", Protein Science, 2005, 14: 1-11.
F.V. Fossella et al., "Phase II Trial of BB-10901 (huN901-DM1) given weekly for four consecutive weeks every 6 weeks in Patients with Relapsed Small Cell Lung Cancer and CD56-Positive Small Cell Carcinoma", ASCO, 2005, Abstract 30765.
Ravi V.J. Chari et al., "Additive and Synergistic Effects of Combination Treatment with huN901-DM1 (BB-10901) and Chemotherapeutic Agents in Small Cell Lung Cancer Xenograft Tumor Models", EORTC 2005, Abstract B-16.
P. Lorigan et al., "Phase I trial of BB-10901 (huN901-DM1) given daily by IV infusion for three consecutive days every three weeks in patients with SCLC and other CD56-positive solid tumors", EORTC, 2006, Abstract 649.
A. Chanan-Khan et al., "Phase I Study of huN901-DM1 (BB10901) in Patients with Relapsed and Relapsed/Refractory CD56-Positive Multiple Myeloma", ASH, Dec. 2006.
A. Chanan-Khan et al., "Phase I Study of IMGN901 (huN901-DM1 or BB-10901) in Patients with Relapsed and Relapsed/Refractory CD56-Positive Multiple Myeloma", ASH, Dec. 2007.
J. McCann et al., "Phase II trial of huN901-DM1 in patients with relapsed small cell lung cancer (SCLC) and CD56-positive small cell carcinoma", Journal of Clinical Oncology, 2007 ASCO Annual Meeting Proceedings Part I., 2007, 25(18S): 18084.
Robert J. Lutz et al., "Efficacy of the HuN901-DM1 Conjugate in Combination with Antineoplastic Agents against Multiple Myeloma Cells in Preclinical Studies", AACR, 2007 Annual Meeting Apr. 2007 (Los Angeles), Abstract 5577.
A. Chanan-Khan et al., "Phase I Study of IMGN901 (huN901-DM1 or BB-10901) Given Weekly for 2 Consecutive Weeks Every 3 Weeks in Patients with Relapsed or Relapsed/Refractory CD56-Positive Multiple Myeloma", ASH, Dec. 2008, Abstract 3689.
P. Woll et al., "Phase I study of IMGN901 (BB-10901) in patients with CD56-positive solid tumors", EORTC-NCI-AACR, 2008, Abstract 510.
Kathleen R. Whiteman et al., "Efficacy of IMGN901 (huN901-DM1) in Combination with Bortezomib and Lenalidomide against Multiple Myeloma Cells in Preclinical Studies", AACR 2008 Annual Meeting Apr. 2008 (San Diego), Abstract 2146.
Kathleen R. Whiteman et al., "Preclinical Evaluation of IMGN901 (huN901-DM1) as a Potential Therapeutic for Ovarian Cancer", AACR, 2008, Abstract 2135.
K. Ishitsuka et al., "Targeting CD56 by the maytansinoid immunoconjugate IMGN901 (huN901-DM1): a potential therapeutic modality implication against natural killer/T cell malignancy", British Journal of Haematology, 2008, 141(1):129-31.
Kathleen R. Whiteman et al., "Combination Therapy with IMGN901 and Lenalidomide Plus Low-Dose Dexamethasone is Highly Effective in Multiple Myeloma Xenograft Models", AACR, 2009, Abstract 2799.
P.J. Woll et al., "Clinical Experience of IMGN901 (BB-10901, huN901-DM1) in Patients with Merkel Cell Carcinoma (MCC)", AACR, 2009, Abstract B237.
A. Chanan-Khan, "Phase I Study of IMGN901, Used as Monotherapy, in Patients with Heavily Pre-Treated CD56-Positive Multiple Myeloma. A Preliminary Safety and Efficacy Analysis", ASH, Dec. 2009.
F.V. Fosella et al., "Clinical Experience of IMGN901 (BB-10901) in Patients with Small Cell Lung Carcinoma (SCLC)", 13th World Conference on Lung Cancer, Jul. 31 to Aug. 4, 2009. (San Francisco, CA).
J. Berdeja et al., "Phase I Study of Lorvotuzumab Mertansine (IMGN901) Used in Combination with Lenalidomide and Dexamethasone in Patients with CD56-Positive Multiple Myeloma. A Preliminary Safety and Efficacy Analysis of the Combination", ASH, 2010, Abstract 1934.
A. Chanan-Khan et al., "Efficacy Analysis from Phase I Study of Lorvotuzumab Mertansine (IMGN901) Used as Monotherapy in Patients with Heavily Pre-Treated CD56-Positive Multiple Myeloma", ASH, 2010, Abstract 1962.
P.J. Woll et al., "Phase I study of lorvotuzumab mertansine (IMGN901) in patients with CD56-positive solid tumors", ESMO, 2010, Abstract 536P.
Olga Ab et al., "Factors determining sensitivity of tumor cells to lorvotuzumab mertansine in vitro", AACR-EORTC-NCI, 2011, San Francisco, CA, Abstract C61.
Kathleen R. Whiteman et al., "Lorvotuzumab mertansine (IMGN901) in combination with standard-of-care paclitaxel/carboplatin therapy is highly active in a preclinical xenograft model of ovarian cancer", AACR, 2011, Abstract 1781.
Anna Skaletskaya et al., "Lorvotuzumab Mertansine (IMGN901) Immune Effector Activity and its Effect on NK Cells", AACR, 2011, Abstract 770.
Christina N. Carrigan et al., The antigen target of lorvotuzumab mertansine (IMGN901), CD56, is expressed at significant levels in Merkel cell carcinoma (MCC), AACR, 2010, Abstract 5335.
Office Action issued in corresponding Russian Application No. RU 2011101461 on Nov. 3, 2011 (in the name of Immunogen Inc.).
L.K. Ovchinnikova et al., "On interaction of medicaments, part II", Journal "Rossiyskie apteki", No. 11/1, 2006.
Extended European Search Report issued in corresponding EP Application No. 09798415.7 on Oct. 15, 2012.
Theirry Facon et al., "Frontline treatment in multiple myeloma patients not eligible for stem-cell transplantation", Best Practice & Research Clinical Haematology, 2007, 20(4): 737-746.
Shaji K. Kumar et al., "Improved survival in multiple myeloma and the impact of novel therapies", Blood, 2008, 111(5): 2516-2520.
H. Ludwig et al., "Advances in the treatment of hematological malignancies: current treatment approaches in multiple myeloma", Annals of Oncology, 2007, 18 (Suppl. 9): ix64-ix70.

\* cited by examiner

Combination of huN901-DM1 with melphalan in Molp-8 multiple myeloma xenografts.

Figure 1B

Table 1. Combination of huN901-DM1 with melphalan in Molp-8 multiple myeloma xenografts.

| Agent | Dosage per injection | Dose schedule | T/C (%) | log cell kill | Conclusions |
|---|---|---|---|---|---|
| huN901-DM1 | 200 µg/kg | qd x 1 | 27 | 0.6 | active |
| Melphalan | 12 mg/kg | qd x 1 | 16 | 0.8 | active |
| Combination | | | 4 | 2.1 | highly active, synergistic |

Combination of huN901-DM1 with thalidomide in Molp-8 multiple myeloma xenografts.

Combination of huN901-DM1 with thalidomide in Molp-8 multiple myeloma xenografts.

Figure 2C

Table 2. Combination of huN901-DM1 with thalidomide in Molp-8 multiple myeloma xenografts.

| Agent | Dosage per injection | Dose schedule | T/C (%) | log cell kill | Conclusions |
|---|---|---|---|---|---|
| HuN901-DM1 | 100 µg/kg | 1qw x 2 | 80 | 0.0 | inactive |
| Thalidomide | 200 mg/kg | 1x daily (11doses total) | 74 | 0.1 | inactive |
| Combination | | | 26 | 0.7 | active, synergistic |
| HuN901-DM1 | 250 µg/kg | 1qw x 2 | 17 | 0.8 | active |
| Thalidomide | 200 mg/kg | 1x daily (11doses total) | 74 | 0.1 | inactive |
| Combination | | | 7 | 1.0 | highly active, additive to synergistic |

Combination of huN901-DM1 with bortezomib in OPM2 multiple myeloma xenografts.

Combination of huN901-DM1 with bortezomib in OPM2 multiple myeloma xenografts.

Figure 3C

Table 3. Combination of huN901-DM1 with bortezomib in OPM2 multiple myeloma xenografts.

| Agent | Dosage per injection | Dose schedule | T/C (%) | log cell kill | Tumor free survivors (day 91) | Conclusions |
|---|---|---|---|---|---|---|
| HuN901-DM1 | 100 µg/kg | qd x 1 | 32.6 | 0.6 | 1/6 | active |
| Bortezomib | 1 mg/kg | 2qw x 1 | 32.6 | 0.5 | 0/6 | active |
| Combination | | | 0.6 | | 6/6 | highly active, synergistic |
| HuN901-DM1 | 200 µg/kg | qd x 1 | 0.0 | 0.8 | 3/6 | highly active |
| Bortezomib | 1 mg/kg | 2qw x 1 | 32.6 | 0.5 | 0/6 | active |
| Combination | | | 0.0 | | 6/6 | highly active, synergistic |

Combination of huN901-DM1 with bortezomib (low-dose) in large H929 multiple myeloma xenografts.

Figure 4B

Table 4a. Combination of huN901-DM1 with low-dose bortezomib in H929 large tumor multiple myeloma xenografts.

| Agent | Dosage per injection | Dose schedule | T/C (%) | Tumor free survivors (day119) | Conclusions |
|---|---|---|---|---|---|
| HuN901-DM1 | 50 µg/kg | qd x 1 | 93 | 0/6 | inactive |
| Bortezomib | 0.5 mg/kg | 2qw x 1 | 100 | 0/6 | inactive |
| Combination | | | 38 | 0/6 | active, synergistic |
| HuN901-DM1 | 100 µg/kg | qd x 1 | 67 | 0/6 | inactive |
| Bortezomib | 0.5 mg/kg | 2qw x 1 | 100 | 0/6 | inactive |
| Combination | | | 17 | 1/6 | active, synergistic |

Combination of huN901-DM1 with bortezomib (high-dose) in large H929 multiple myeloma xenografts.

Figure 4D

Table 4b. Combination of huN901-DM1 with high-dose bortezomib in H929 large tumor multiple myeloma xenografts.

| Agent | Dosage per injection | Dose schedule | T/C (%) | Tumor free survivors (day 119) | Conclusions |
|---|---|---|---|---|---|
| HuN901-DM1 | 50 µg/kg | qd x 1 | 93 | 0/6 | inactive |
| Bortezomib | 1.0 mg/kg | 2qw x 1 | 11 | 1/6 | active |
| Combination | | | 7 | 2/6 | highly active, synergistic |
| HuN901-DM1 | 100 µg/kg | qd x 1 | 67 | 0/6 | inactive |
| Bortezomib | 1.0 mg/kg | 2qw x 1 | 11 | 1/6 | active |
| Combination | | | 0 | 5/6 | highly active, synergistic |

Combination of huN901-DM1 with lenalidomide in OPM2 multiple myeloma xenografts.

Figure 5B

Table 5. Combination of huN901-DM1 with lenalidomide in OPM2 multiple myeloma xenografts

| Agent | Dosage per injection | Dose schedule | T/C (%) | log cell kill | Tumor free survivors (Day 119) | Conclusions |
|---|---|---|---|---|---|---|
| HuN901-DM1 | 200 µg/kg | qd x 1 | 25.5 | 0.9 | 0/5 | Active |
| Lenalidomide | 100 mg/kg | qd x 5 x 2w | 28 | 0.9 | 0/5 | Active |
| Combination | | | 1.4 | 1.7 | 1/5 | Highly Active, Synergistic |

Schedule dependency of the anti-tumor effect of the combination of huN901-DM1 with bortezomib.

Triple combination of huN901-DM1 with lenalidomide plus low-dose dexamethasone in MOLP-8 multiple myeloma xenografts.

Figure 7B

Table 7. Triple combination of huN901-DM1 with lenalidomide plus low-dose dexamethasone in MOLP-8 multiple myeloma xenografts

| Treatment | Agent | Dosage per injection | Dose schedule | T/C (%) | log cell kill | Regressions | | Conclusions |
|---|---|---|---|---|---|---|---|---|
| | | | | | | Partial | Complete | |
| Single-Agent huN901-DM1 | huN901-DM1 | 150 µg/kg | 1qw x 2 | 33 | 0.5 | 0/6 | 0/6 | active |
| Two-Agent Combination len/dex | lenalidomide | 100 mg/kg | qd x 5 x 2w | 33 | 0.5 | 0/6 | 0/6 | active |
| | dexamethasone | 1.5 mg/kg | 1qw x 2 | | | | | |
| Triple-Agent Combination huN901-DM1/len/dex | | | | 0 | 1.4 | 6/6 | 4/6 | highly active |

Triple combination of huN901-DM1 with lenalidomide plus low-dose dexamethasone results in a significant increase in tumor-cell apoptosis in MOLP-8 multiple myeloma xenografts.

Triple combination of huN901-DM1 with lenalidomide plus low-dose dexamethasone results in a significant increase in tumor-cell apoptosis in MOLP-8 multiple myeloma xenografts.

SYNERGISTIC EFFECTS

This application claims the benefit of U.S. provisional application No. 61/061,886, filed Jun. 16, 2008, the entire disclosure of which is expressly incorporated herein by reference.

FIELD OF INVENTION

The present invention relates to anticancer combinations, pharmaceutical compositions comprising the same, and the use thereof in the treatment of cancer. In particular, the present invention is based on the discovery that the administration of a combination comprising at least one cell binding agent drug conjugate (e.g., an immunoconjugate) and one or more chemotherapeutic agent(s) selected from proteasome inhibitors (e.g., bortezomib), immunomodulatory agents/anti-angiogenic agents (e.g., thalidomide or lenalidomide), and DNA alkylating agents (e.g., melphalan), with the optional further addition of a corticosteroid (e.g., dexamethasone) has therapeutic synergy or improves the therapeutic index in the treatment of cancer over the anticancer agent(s) alone. The present invention also provides methods of modulating the growth of selected cell populations, such as cancer cells, by administering a therapeutically effective amount of such combination.

BACKGROUND

Preclinically, the effect of a combination of anti-cancer drugs can be studied in vitro on cell lines or in vivo with different tumor models. Typically, anti-cancer drugs that have different mechanisms of killing, i.e. have different targets in the cell, are combined. In such experimental systems, it was observed that two anti-cancer drugs with independent targets (mutually exclusive drugs) either behave in an additive, synergistic, or antagonistic manner. Chou and Talalay (*Adv. Enzyme Regul.* 1984, 22:27-55) developed a mathematical method that could accurately describe the experimental findings in a qualitative and quantitative manner. For mutually exclusive drugs, they showed that the generalized isobol equation applies for any degree of effect (see page 52 in Chou and Talalay). An isobol or isobologram is the graphic representation of all dose combinations of two drugs that have the same degree of effect, for example combinations of two cytotoxic drugs will affect the same degree of cell kill, such as 20% or 50% of cell kill. The equation is valid for any degree of effect and the graphic representation will have the same shape (page 54, line 1, in Chou and Talalay), which is presented in FIG. 11 D (page 5 in Chou and Talalay). In isobolograms, a straight line indicates additive effects, a concave curve (curve below the straight line) represents synergistic effects, and a convex curve (curve above the straight line) represents antagonistic effects. These curves also show that a combination of two mutually exclusive drugs will show the same type of effect over the whole concentration range, either the combination is additive, synergistic, or antagonistic. Most drug combinations show an additive effect. In some instances however, the combinations show less or more than an additive effect. These combinations are called antagonistic or synergistic, respectively. Antagonistic or synergistic effects are unpredictable, and are unexpected experimental findings. A combination manifests therapeutic synergy if it is therapeutically superior to one or other of the constituents used at its optimum dose. See T. H. Corbett et al., Cancer Treatment Reports, 66, 1187 (1982). Tallarida R J (J Pharmacol Exp Ther. 2001 September; 298 (3):865-72) also notes "Two drugs that produce overtly similar effects will sometimes produce exaggerated or diminished effects when used concurrently. A quantitative assessment is necessary to distinguish these cases from simply additive action".

That the unpredictability of antagonistic or synergistic effects is well known to one of skill in the art is demonstrated in several other studies, such as, by Knight et al. See BMC Cancer 2004, 4:83. In this study, the authors measured the activity of gefitinib (also known as Iressa) alone or in combination with different cytotoxic drugs (cisplatin, gemcitabine, oxaliplatin and treosulfan) against a variety of solid tumors including breast, colorectal, esophageal and ovarian cancer, carcinoma of unknown primary site, cutaneous and uveal melanoma, non-small cell lung cancer (NSCLC) and sarcoma.

They discovered that there was heterogeneity in the degree of tumor growth inhibition (TGI) observed when tumors were tested against single agent gefitinib. In 7% (6/86) of tumors considerable inhibition of tumor growth was observed, but most showed a more modest response resulting in a low degree of TGI. Interestingly, gefitinib had both positive and negative effects when used in combination with different cytotoxic drugs. In 59% (45/76) of tumors tested, the addition of gefitinib appeared to potentiate the effect of the cytotoxic agent or combination (of these, 11% (5/45) had a >50% decrease in their $Index_{SUM}$). In 38% of tumors (29/76), the TGI was decreased when the combination of gefitinib+cytotoxic drug was used in comparison to the cytotoxic drug alone. In the remaining 3% (2/76) there was no change observed.

The authors conclude that gefitinib in combination with different cytotoxic agents (cisplatin; gemcitabine; oxaliplatin; treosulfan and treosulfan+gemcitabine) is a double-edged sword: their effect on growth rate may make some tumors more resistant to concomitant cytotoxic chemotherapy, while their effect on cytokine-mediated cell survival (anti-apoptotic) mechanisms may potentiate sensitivity to the same drugs in tumors from other individuals. See conclusion on page 7; see also FIG. 3. Knight et al., BMC Cancer 2004, 4:83.

Thus, this study proves that two compounds, which are known to be useful for the same purpose, are combined for that purpose, may not necessary perform the same purpose.

Finding highly efficacious combinations, i.e., synergistic mixtures, of active agents is challenging however. Serendipity is not a valid route as the number of potential combinations of agents is staggeringly large. For example, there are trillions of possible 5 fold combinations of even a relatively small palette of 5000 potential agents. The other normal discovery strategy of deducing potential combinations from knowledge of mechanism is also limited in its potential because many biological end points of living organisms are affected by multiple pathways. These pathways are often not known, and even when they are, the ways in which the pathways interact to produce the biological end effect are often unknown.

Previously, we demonstrated synergistic combination of a maytansinoid immunoconjugate comprising a maytansinoid compound linked to a monoclonal antibody with that of a taxane compound, an epothilone compound, a platinum compound, an epipodophyllotoxin compound and a camptothecin compound.

Synergistic uses of combination of drugs even if previously demonstrated do not obviate the need to look for new synergistic combinations because synergistic effects are unpredictable and because these are unexpected experimental findings. For example, in treatment of autoimmune deficiency syndrome (AIDS), which involved highly active anti-retroviral therapy (HAART), it was believed that cocktail of inhibitors of HIV-1 viral reverse transcriptase (RT) and the viral protease (PR), exhibit synergistic inhibition of viral replication. Later on, intriguingly, synergy was also observed within two classes of RT inhibitors—that is, the nucleoside RT inhibitors (NRTIs) showed synergy with the nonnucleoside RT inhibitors (NNRTIs) in the absence of PR inhibitors. For example, NRTI, AZT (zidovudine) and the NNRTI, nevirapin exhibit synergy when given in combination (Basavapathruni A et al., J. Biol. Chem., Vol. 279, Issue 8, 6221-6224, Feb. 20, 2004). Thus, there is still a need for finding drug combinations that show synergism and can be effectively used for the treatment and prevention of debilitating diseases such as cancer.

SUMMARY OF THE INVENTION

The present invention is based on the discovery that the administration of a combination comprising at least one cell binding agent drug conjugate (e.g., an immunoconjugate), hereinafter referred to as "Conjugate" and at least one chemotherapeutic agent selected from proteasome inhibitors (e.g., bortezomib), immunomodulatory agents/anti-angiogenic agents (e.g., thalidomide or lenalidomide), and DNA alkylating agents (e.g., melphalan), optionally further combined with a corticosteroid (e.g., dexamethasone) has therapeutic synergy or improves the therapeutic index in the treatment of cancer over the immunoconjugate used alone, or the chemotherapeutic agent used alone or in combination with another chemotherapeutic agent, without the addition of the immunoconjugate.

In a preferred embodiment, the conjugate and the chemotherapeutic agent(s) are administered in combination with a corticosteroid, such as, dexamethasone. For example, an immunoconjugate, such as, humanized antibody N901-maytansinoid conjugate (huN901-DM1) is administered in combination with thalidomide/dexamethasone, lenalidomide/dexamethasone or bortezomib/dexamethasone, wherein such combination has therapeutic synergy or improves the therapeutic index in the treatment of cancer over the immunoconjugate used alone, the chemotherapeutic agent used alone or in combination with another chemotherapeutic agent, without the addition of the immunoconjugate.

In another embodiment, two or more chemotherapeutic agents are used in combination with the immunoconjugate. For example, bortezomib and lenalidomide are used in combination with huN901 maytansinoid conjugate, in presence or absence of a corticosteroid, such as, dexamethasone, wherein such combination has therapeutic synergy or improves the therapeutic index in the treatment of cancer over the immunoconjugate used alone, the chemotherapeutic agent used alone or in combination with another chemotherapeutic agent, without the addition of the immunoconjugate.

The term "therapeutic synergy," as used herein, means combination of a conjugate and one or more chemotherapeutic agent(s) having a therapeutic effect greater than the additive effect of the combination of a conjugate and or one or more chemotherapeutic agent.

Another object of the present invention describes methods of ameliorating or treating cancer in a patient in need thereof by administering to the patient a therapeutically effective amount of at least one conjugate (e.g., immunoconjugate) and one or more chemotherapeutic agents, (e.g., a proteasome inhibitor, an immunomodulatory agent/anti-angiogenic agent, or a DNA alkylating agent), with the optional further addition of a corticosteroid (e.g. dexamethasone) such that the combination has therapeutic synergy or improves the therapeutic index in the treatment of cancer over the anticancer agent(s) used alone or in combination, without the addition of the immunoconjugate.

In a further aspect, the present invention provides a pharmaceutical composition comprising an effective amount of a conjugate (e.g., immunoconjugate) and one or more of a chemotherapeutic agent (e.g., a proteasome inhibitor, an immunomodulatory agent/anti-angiogenic agent, or a DNA alkylating agent), optionally together with a pharmaceutically acceptable carrier.

The present invention still further provides the use of a conjugate (e.g., immunoconjugate) and a chemotherapeutic agent (e.g., a proteasome inhibitor, an immunomodulatory agent/anti-angiogenic agent, or a DNA alkylating agent) with the optional addition of a corticosteroid, for the preparation of a medicament for combination therapy by simultaneous, sequential or separate administration in the treatment of cancer or any disease resulting from abnormal proliferation of cells. For example, the conjugate and the drug(s) can be administered on the same days or different days, using the optimal dosing schedule for each agent. For example, in one embodiment, the two compounds could be administered within ten days of each other, in another embodiment, within five days of each other, and yet in another embodiment within twenty-four hours of each other, or even simultaneously. Alternatively, huN901-DM1, the chemotherapeutic agent(s), corticosteroid, or any combination thereof could be administered every other day, on alternate days, on a weekly basis or time period that ranges between day 0 and 7 (e.g., day 0, 1, 2, 3, 4, 5, 6, or 7) or ranges between 0 and 4 weeks (e.g., 0, 1, 2, 3 or 4 weeks, including days that may add up between 1 or more weeks). In some cases, it may be preferred that a chemotherapeutic agent is administered first followed by conjugate. For example, bortezomib is administered on day zero followed by huN901-DM1 on day 3. The drug administration can be determined by one of skill in the art as the clinical situation warrants.

The present invention also describes methods of modulating the growth of selected cell populations, such as cancer cells, by administering a therapeutically effective amount of at least one conjugate (e.g., an immunoconjugate) and one or more chemotherapeutic drug(s) (e.g., a proteasome inhibitor, an immunomodulatory agent/anti-angiogenic agent, or a DNA alkylating agent), with the optional addition of a corticosteroid, such that the combination has therapeutic synergy or improves the therapeutic index in the treatment of cancer over the anticancer agent(s) used alone or in combination, without the addition of the immunoconjugate. The conjugate can comprise a cell binding agent and at least one therapeutic agent for killing selected cell populations.

These and other aspects of the present invention are described in detail herein.

BRIEF DESCRIPTION OF DRAWINGS

FIG. 1B is a table (Table 1) showing the data.

FIGS. 2A, 2B and 2C shows a combination of huN901-DM1 with thalidomide in Molp-8 multiple myeloma xenografts. FIG. 2A shows data for a combination of 100 µg/kg huN901-DM1 plus 100 mg/kg thalidomide. FIG. 2B shows data for a combination of 250 µg/kg huN901-DM1 plus 100 mg/kg thalidomide. FIG. 2C is a table (Table 2) showing the data.

FIGS. 3A, 3B and 3C shows a combination of huN901-DM1 with bortezomib in OPM2 multiple myeloma xenografts. FIG. 3A shows data for a combination with 100 μg/kg huN901-DM1. FIG. 3B shows data for a combination with 200/kg huN901-DM1. FIG. 3C is a table (Table 3) showing the data.

FIG. 4B is a table (Table 4a) showing the data.

FIG. 4D is a table (Table 4b) showing the data.

FIG. 5B is a table (Table 5) showing the data.

FIG. 7B is a table (Table 7a) showing the data.

DETAILED DESCRIPTION OF THE INVENTION

Figure 1A:
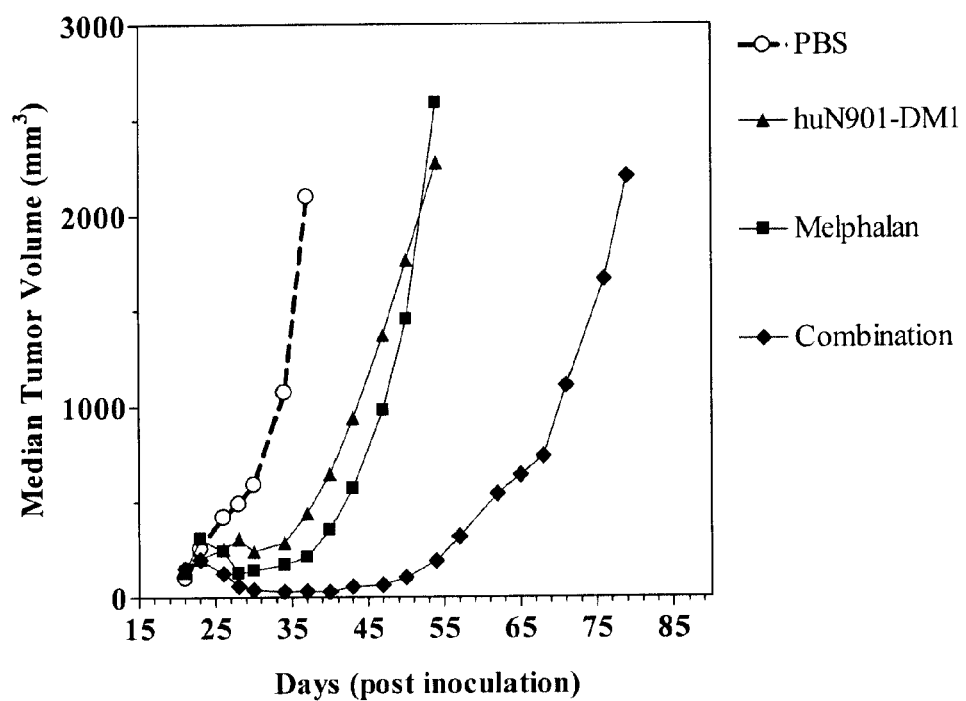
FIG. 1A shows a combination of huN901-DM1 with melphalan in Molp-8 multiple myeloma xenografts.

The present invention is based on the unexpected discovery that the administration of at least one conjugate (e.g., immunoconjugate) and at least one chemotherapeutic drug (e.g., a proteasome inhibitor, an immunomodulatory agent/anti-angiogenic agent, or a DNA alkylating agent), with the optional further addition of a corticosteroid (dexamethasone), has therapeutic synergy or improves the therapeutic index in the treatment of cancer over the immunoconjugate alone, the chemotherapeutic agent used alone or in combination with another chemotherapeutic agent, without the addition of the immunoconjugate. Appropriate conjugates and chemotherapeutic agents are described herein.

Conjugates

The conjugates of the present invention comprise at least one therapeutic agent for killing selected cell populations linked to a cell binding agent.

The therapeutic agent for killing selected cell populations is preferably an anti-mitotic agent. Anti-mitotic agents, which are known in the art, kill cells by inhibiting tubulin polymerization and, therefore, microtubule formation. Any anti-mitotic agent known in the art can be used in the present invention, including, for example, maytansinoids, Vinca alkaloids, dolastatins, auristatins, cryptophycins, tubulysin, and/or any other agent that kills cells by inhibiting tubulin polymerization. Preferably, the anti-mitotic agent is a maytansinoid.

The cell binding agent can be any suitable agent that binds to a cell, typically and preferably an animal cell (e.g., a human cell). The cell binding agent preferably is a peptide or a polypeptide. Suitable cell binding agents include, for example, antibodies (e.g., monoclonal antibodies and fragments thereof), lymphokines, hormones, growth factors, nutrient-transport molecules (e.g., transferrin). Therapeutic agents for killing selected cell populations and cell binding agents that could be part of the immunoconjugate are described below in greater detail.

Maytansinoids

Maytansinoids that can be used in the present invention are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamitocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315, 929) (isolated from *Trewia nudiflora*);

(6) C-18-N-demethyl (U.S. Pat. Nos. 4,362,663 and 4,322, 348) (prepared by the demethylation of maytansinol by *Streptomyces*); and (7) 4,5-deoxy (U.S. Pat. No. 4,371,533) (prepared by the titanium trichloride/LAH reduction of maytansinol).

The synthesis of thiol-containing maytansinoids useful in the present invention is fully disclosed in U.S. Pat. Nos. 5,208,020, 5,416,064, 6,333,410, 7,276,497 and 7,301,019)

Maytansinoids with a thiol moiety at the C-3 position, the C-14 position, the C-15 position or the C-20 position are all expected to be useful. The C-3 position is preferred and the C-3 position of maytansinol is especially preferred. Also preferred are an N-methyl-alanine-containing C-3 thiol moiety maytansinoid, and an N-methyl-cysteine-containing C-3 thiol moiety maytansinoid, and analogues of each.

Specific examples of N-methyl-alanine-containing C-3 thiol moiety maytansinoid derivatives useful in the present invention are represented by the formulae M1, M2, M3, M6 and M7.

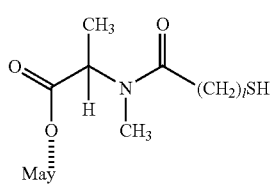

M1 wherein:
l is an integer of from 1 to 10; and
may is a maytansinoid.

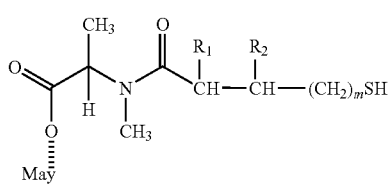

M2 wherein:
$R_1$ and $R_2$ are H, $CH_3$ or $CH_2CH_3$, and may be the same or different;
m is 0, 1, 2 or 3; and
may is a maytansinoid.

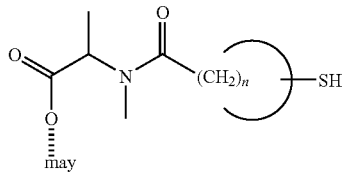

M3 wherein:
n is an integer of from 3 to 8; and
may is a maytansinoid.

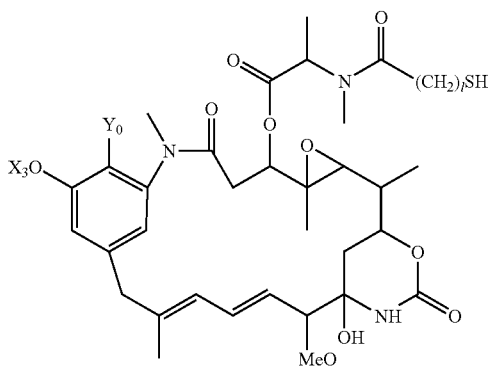

M6 wherein:
l is 1, 2 or 3;
$Y_0$ is Cl or H; and
$X_3$ is H or $CH_3$.

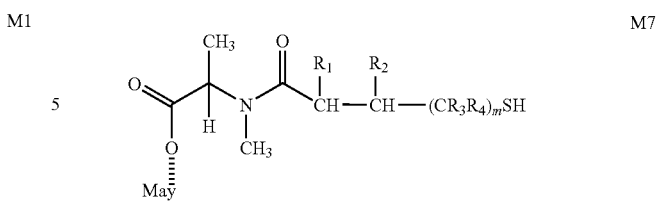

M7 wherein:
$R_1$, $R_2$, $R_3$, $R_4$ are H, $CH_3$ or $CH_2CH_3$, and may be the same or different;
m is 0, 1, 2 or 3; and
may is a maytansinoid.

Specific examples of N-methyl-cysteine-containing C-3 thiol moiety maytansinoid derivatives useful in the present invention are represented by the formulae M4 and M5.

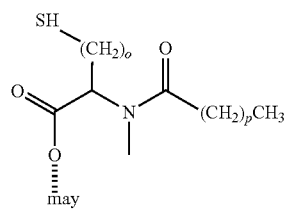

M4 wherein:
o is 1, 2 or 3;
p is an integer of 0 to 10; and
may is a maytansinoid.

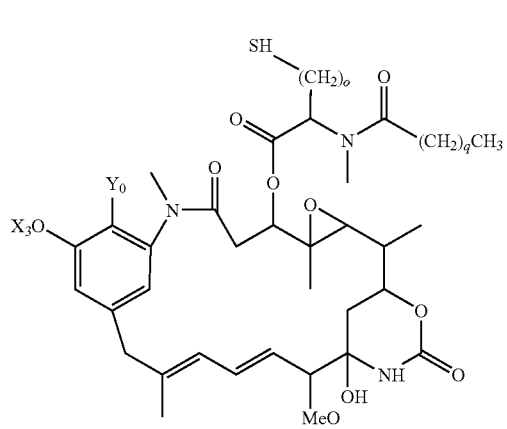

M5 wherein:
o is 1, 2 or 3;
q is an integer of from 0 to 10;
$Y_0$ is Cl or H; and
$X_3$ is H or $CH_3$.

Preferred maytansinoids are those described in U.S. Pat. Nos. 5,208,020; 5,416,064; 6,333,410; 6,441,163; 6,716,821; RE39,151 and U.S. Pat. No. 7,276,497.

Vinca alkaloid compounds (e.g., vincristine), dolastatin compounds, and cryptophycin compounds are describe in detail in WO01/24763. Auristatin include auristatin E, auristatin EB (AEB), auristatin EFP (AEFP), monomethyl auristatin E (MMAE) are described in U.S. Pat. No. 5,635, 483, Int. J. Oncol. 15:367-72 (1999); Molecular Cancer Therapeutics, vol. 3, No. 8, pp. 921-932 (2004); U.S. application Ser. No. 11/134,826. US Publication Nos. 20060074008, 2006022925. Tubulysin compounds are described in US Publication Non. 20050249740. Many of the agents listed under this heading, if intended, can also be used as chemotherapeutic agents.

Cell Binding Agents

The cell-binding agents used in this invention are proteins (e.g., immunoglobulin and non-immunoglobulin proteins) that bind specifically to target antigens on cancer cells. These cell-binding agents include the following:

antibodies including:
  resurfaced antibodies (U.S. Pat. No. 5,639,641);
  humanized or fully human antibodies (Humanized or fully human antibodies are selected from, but not limited to, huMy9-6, huB4, huC242, huN901, DS6, CD38, IGF-IR, CNTO 95, B-B4, trastuzumab, bivatuzumab, sibrotuzumab, pertuzumab and rituximab (see, e.g., U.S. Pat. Nos. 5,639,641, 5,665,357, and 7,342,110; U.S. Provisional Patent Application No. 60/424,332, International Patent Application WO 02/16,401, U.S. Patent Publication Number 20060045877, U.S. Patent Publication Number 20060127407, U.S. Patent Publication No. 20050118183, Pedersen et al., (1994) *J. Mol. Biol.* 235, 959-973, Roguska et al., (1994) *Proceedings of the National Academy of Sciences*, Vol 91, 969-973, Colomer et al., *Cancer Invest.*, 19: 49-56 (2001), Heider et al., *Eur. J. Cancer*, 31A: 2385-2391 (1995), Welt et al., *J. Clin. Oncol.*, 12: 1193-1203 (1994), and Maloney et al., *Blood*, 90: 2188-2195 (1997)); and
  epitope binding fragments of antibodies such as sFv, Fab, Fab', and F(ab')$_2$ (Parham, *J. Immunol.* 131:2895-2902 (1983); Spring et al, *J. Immunol.* 113:470-478 (1974); Nisonoff et al, *Arch. Biochem. Biophys.* 89:230-244 (1960)).

Additional cell-binding agents include other cell-binding proteins and polypeptides exemplified by, but not limited to:

Ankyrin repeat proteins (DARPins; Zahnd et al., *J. Biol. Chem.*, 281, 46, 35167-35175, (2006); Binz, H. K., Amstutz, P. & Pluckthun, A. (2005) *Nature Biotechnology*, 23, 1257-1268) or ankyrin-like repeats proteins or synthetic peptides described, for example, in U.S. Patent Publication No. 20070238667; U.S. Pat. No. 7,101,675; WO/2007/147213; and WO/2007/062466);

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens; and growth factors and colony-stimulating factors such as EGF, TGF-α, IGF-1, G-CSF, M-CSF and GM-CSF (Burgess, *Immunology Today* 5:155-158 (1984)).

Where the cell-binding agent is an antibody (e.g., a single chain antibody, an antibody fragment that binds to the target cell, a monoclonal antibody, a single chain monoclonal antibody, or a monoclonal antibody fragment thereof, a chimeric antibody, a chimeric antibody fragment thereof, a domain antibody, a domain antibody fragment thereof, a resurfaced antibody, a resurfaced single chain antibody, or a resurfaced antibody fragment thereof, a human antibody or a human antibody fragment thereof, a humanized antibody or a resurfaced antibody, a humanized single chain antibody, or a humanized antibody fragment thereof), it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, tarnsferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD23, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; and fragments of any of the above-listed polypeptides, antibody mimics Adnectins (US appl 20070082365), or an antibody which binds to one or more tumor-associated antigens or cell-surface receptors disclosed in US Publication No. 20080171040 or US Publication No. 20080305044 and are incorporated in their entirety by reference.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

Preferred antigens for antibodies encompassed by the present invention include CD proteins such as CD2, CD3, CD4, CD5, CD6, CD8, CD11, CD14, CD18, CD19, CD20, CD 21, CD22, CD 25, CD26, CD28, CD30, CD33, CD36, CD37, CD38, CD40, CD44, CD52, CD55, CD56, CD70, CD79, CD80, CD81, CD103, CD105, CD134, CD137, CD138, and CD152; members of the ErbB receptor family such as the EGF receptor, HER2, HER3 or HER4 receptor; cell adhesion molecules such as LFA-1, Mac1, p150.95, VLA-4, ICAM-1, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C etc. The most preferred targets herein are IGF-IR, CanAg, EphA2, MUC1, MUC16, VEGF, TF, CD19, CD20, CD22, CD33, CD37, CD38, CD40, CD44, CD56, CD138, CA6, Her2/neu, EpCAM, CRIPTO (a protein produced at elevated levels in a majority of human breast cancer cells), darpins, alpha$_v$/beta$_3$ integrin, alpha$_v$/beta$_5$ integrin, alpha$_v$/beta$_6$ integrin, TGF-β, CD11a, CD18, Apo2 and C242 or an antibody which binds to one or more tumor-associated antigens or cell-surface receptors disclosed in US Publication No. 20080171040 or US Publication No. 20080305044 and are incorporated in their entirety by reference.

Preferred antigens for antibodies encompassed by the present invention also include CD proteins such as CD3, CD4, CD8, CD19, CD20, CD34, CD37, CD38, CD46, CD56 and CD138; members of the ErbB receptor family such as the EGF receptor, HER2, HER3 or HER4 receptor; cell adhesion molecules such as LFA-1, Mac1, p150.95, VLA-4, ICAM-1, VCAM, EpCAM, alpha4/beta7 integrin, and alpha v/beta3 integrin including either alpha or beta subunits thereof (e.g. anti-CD11a, anti-CD18 or anti-CD11b antibodies); growth factors such as VEGF; tissue factor (TF); TGF-β; alpha interferon (alpha-IFN); an interleukin, such as IL-8; IgE; blood group antigens Apo2, death receptor; flk2/flt3 receptor; obesity (OB) receptor; mpl receptor; CTLA-4; protein C, etc. The most preferred targets herein are IGF-IR, CanAg, EGF-R, EphA2, MUC1, MUC16, VEGF, TF, CD19, CD20, CD22, CD33, CD37, CD38, CD40, CD44, CD56, CD138, CA6, Her2/neu, CRIPTO (a protein produced at elevated levels in a majority of human breast cancer cells), alpha$_v$/beta$_3$ integrin, alpha$_v$/beta$_5$ integrin, TGF-β, CD11a, CD18, Apo2, EpCAM and C242.

Monoclonal antibody techniques allow for the production of specific cell-binding agents in the form of monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; Liming et al, WO 99/06587.)

Selection of the appropriate cell-binding agent is a matter of choice that depends upon the particular cell population that is to be targeted, but in general monoclonal antibodies and epitope binding fragments thereof are preferred, if an appropriate one is available.

For example, the monoclonal antibody My9 is a murine IgG$_{2a}$ antibody that is specific for the CD33 antigen found on Acute Myeloid Leukemia (AML) cells (Roy et al. *Blood* 77:2404-2412 (1991)) and can be used to treat AML patients. Similarly, the monoclonal antibody anti-B4 is a murine IgG$_1$ that binds to the CD19 antigen on B cells (Nadler et al, *J. Immunol.* 131:244-250 (1983)) and can be used if the target cells are B cells or diseased cells that express this antigen such as in non-Hodgkin's lymphoma or chronic lymphoblastic leukemia. The antibody N901 is a murine monoclonal IgG$_1$ antibody that binds to CD56 found on small cell lung carcinoma cells and on cells of other tumors of neuroendocrine origin (Roy et al. *J. Nat. Cancer Inst.* 88:1136-1145 (1996)); huC242 is an antibody that binds to the CanAg antigen; Trastuzumab is an antibody that binds to HER2/neu; and anti-EGF receptor antibody binds to EGF receptor.

Chemotherapeutic Agents

Drugs that can be used in the present invention include chemotherapeutic agents. "Chemotherapeutic agent" is a chemical compound useful in the treatment of cancer. Preferred examples of chemotherapeutic agents are proteasome inhibitors, immunomodulatory agents, anti-angiogenic agents, alkylating agents or combinations thereof.

Proteasome Inhibitors

Proteasome inhibitors are drugs that block the action of proteasomes, cellular complexes that break down proteins. In one embodiment of the present invention, the proteasome inhibitor is selected from a group comprising: a) naturally occurring proteasome inhibitors comprising: peptide derivatives which have a C-terminal expoxy ketone structure, β-lactone-derivatives, aclacinomycin A, lactacystin, clastolactacystein; b) synthetic proteasome inhibitors comprising: modified peptide aldehydes such as N-carbobenzoxy-L-leucinyl-L-leucinyl-L-leucinal (also referred to as MG132 or zLLL), or the boronic acid derivative of MG232, N-carbobenzoxy-Leu-Nva-H (also referred to as MG115), N-acetyl-L-leucinyl-L-leucinyl-L-norleucinal (also referred to as LLnL), N-carbobenzoxy-Ile-Glu(OBut)-Ala-Leu-H (also referred to as PS1); c) peptides comprising: an α,β-epoxyketone-structure, vinyl-sulfones such as, carbobenzoxy-L-leucinyl-L-leucinyl-L-leucin-vinyl-sulfone or, 4-hydroxy-5-iodo-3-nitrophenylacetyl-L-leucinyl-L-leucinyl-L-leucin-vinyl-1-sulfone (NLVS); d) Glyoxal- or boric acid residues such as: pyrazyl-CONH(CHPhe)CONH(CHisobutyl)B(OH)$_2$ and dipeptidyl-boric-acid derivatives; e) Pinacol-esters such as: benzyloxycarbonyl(Cbz)-Leu-leuboro-Leu-pinacol-ester. Proteasome inhibitors described in Am J Clin Pathol 116(5): 637-646, 2001 or the U.S. application Ser. No. 10/522,706 (filed Jul. 31, 2003) are also encompassed to be within the vision of this present invention. In a preferred embodiment, the proteasome inhibitor is PS-341/bortezomib (Velcade™).

Immunomodulatory Agents

By "immunomodulatory drugs or agents", it is meant, e.g., agents which act on the immune system, directly or indirectly, e.g., by stimulating or suppressing a cellular activity of a cell in the immune system, e.g., T-cells, B-cells, macrophages, or antigen presenting cells (APC), or by acting upon components outside the immune system which, in turn, stimulate, suppress, or modulate the immune system, e.g., hormones, receptor agonists or antagonists, and neurotransmitters; immunomodulators can be, e.g., immunosuppressants or immunostimulants. By "anti-inflammatory drugs", it is meant, e.g., agents which treat inflammatory responses, i.e., a tissue reaction to injury, e.g., agents which treat the immune, vascular, or lymphatic systems.

Anti-inflammatory or immunomodulatory drugs or agents suitable for use in this invention include, but are not limited to, interferon derivatives, e.g., betaseron, β-interferon; prostane derivatives, e.g., compounds disclosed in PCT/DE93/0013, e.g., iloprost, cicaprost; glucocorticoid, e.g., cortisol, prednisolone, methylprednisolone, dexamethasone; immunsuppressives, e.g., cyclosporine A, FK-506, methoxsalene, thalidomide, sulfasalazine, azathioprine, methotrexate; lipoxygenase inhibitors, e.g., zileutone, MK-886, WY-50295, SC-45662, SC-41661A, BI-L-357; leukotriene antagonists, e.g., compounds disclosed in DE 40091171 German patent application P 42 42 390.2; WO 9201675; SC-41930; SC-50605; SC-51146; LY 255283 (D. K. Herron et al., FASEB J. 2: Abstr. 4729, 1988); LY 223982 (D. M. Gapinski et al. J. Med. Chem. 33: 2798-2813, 1990); U-75302 and analogs, e.g., described by J. Morris et al., Tetrahedron Lett. 29: 143-146, 1988, C. E. Burgos et al., Tetrahedron Lett. 30: 5081-5084, 1989; B. M. Taylor et al., Prostaglandins 42: 211-224, 1991; compounds disclosed in U.S. Pat. No. 5,019,573; ONO-LB-457 and analogs, e.g., described by K. Kishikawa et al., Adv. Prostagl. Thombox. Leukotriene Res. 21: 407-410, 1990; M. Konno et al., Adv. Prostagl. Thrombox. Leukotriene Res. 21: 411-414, 1990; WF-11605 and analogs, e.g., disclosed in U.S. Pat. No. 4,963,583; compounds disclosed in WO 9118601, WO 9118879; WO 9118880, WO 9118883, antiinflammatory substances, e.g., NPC 16570, NPC 17923 described by L. Noronha-Blab. et al., Gastroenterology 102 (Suppl.): A 672, 1992; NPC 15669 and analogs described by R. M. Burch et al., Proc. Nat. Acad. Sci. USA 88: 355-359, 1991; S. Pou et al., Biochem. Pharmacol. 45: 2123-2127, 1993; peptide derivatives, e.g., ACTH and analogs; soluble TNF-receptors; TNF-antibodies; soluble receptors of interleukines, other cytokines, T-cell-proteins; antibodies against receptors of interleukins, other cytokines, and T-cell-proteins. Further Examples of immunomodulatory agents include, but are not limited to, methothrexate, leflunomide, cyclophosphamide, cyclosporine A, and macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. For clarification regarding T cell receptor modulators and cytokine receptor modulators see Section 3.1. Examples of T cell receptor modulators include, but are not limited to, anti-T cell receptor antibodies (e.g., anti-CD4 monoclonal antibodies, anti-CD3 monoclonal antibodies, anti-CD8 monoclonal antibodies, anti-CD40 ligand monoclonal antibodies, anti-CD2 monoclonal antibodies) and CTLA4-immunoglobulin. Examples of cytokine receptor modulators include, but are not limited to, soluble cytokine receptors (e.g., the extracellular domain of a TNF-alpha receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-alpha, interferon (IFN)-alpha, IFN-beta, IFN-gamma, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-alpha antibodies, anti-IL-1β antibodies, anti-IL-6 antibodies, and anti-IL-12 antibodies). Agents listed in the U.S. patent application Ser. No. 11/454,559 (filed Jun. 16, 2006). Preferred immunomodulatory drugs are those that are effective for the treatment of multiple myeloma, blood, plasma, or bone-related cancers. In a preferred embodiment, the immunomodulatory agent is selected from thalidomide (Thalomid) and lenalidomide (Revlimid).

Anti-Angiogenic Agents

Anti-angiogenic agents include, but are not limited to, receptor tyrosine kinase inhibitors (RTKi), described in further detail in U.S. patent application Ser. No. 11/612,744 (filed Dec. 19, 2006) or in Ser. No. 10/443,254 (filed May 22, 2003); angiostatic cortisenes; MMP inhibitors; integrin inhibitors; PDGF antagonists; antiproliferatives; HIF-1 inhibitors; fibroblast growth factor inhibitors; epidermal growth factor inhibitors; TIMP inhibitors; insulin-like growth factor inhibitors; TNF inhibitors; antisense oligonucleotides; anti-VEGF antibody, VEGF trap, NSAID, steroids, SiRNA etc., and prodrugs of any of the aforementioned agents. Other agents which will be useful in the compositions and methods of the invention include anti-VEGF antibody (i.e., bevacizumab or ranibizumab); VEGF trap; siRNA molecules, or a mixture thereof, targeting at least two of the tyrosine kinase receptors; glucocorticoids (i.e., dexamethasone, fluoromethalone, medrysone, betamethasone, triamcinolone, triamcinolone acetonide, prednisone, prednisolone, hydrocortisone, rimexolone, and pharmaceutically acceptable salts thereof, prednicarbate, deflazacort, halomethasone, tixocortol, prednylidene (21-diethylaminoacetate), prednival, paramethasone, methylprednisolone, meprednisone, mazipredone, isoflupredone, halopredone acetate, halcinonide, formocortal, flurandrenolide, fluprednisolone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, and deacylcortivazol oxetanone); Naphthohydroquinone antibiotics (i.e., Rifamycin); and NSAIDs (i.e., nepafenac, amfenac). In a preferred embodiment, the anti-angiogenic agent is selected from thalidomide (Thalomid) and lenalidomide (Revlimid). Many of the anti-angiogenic agents, such as lenalidomide and thalidomide, also act as immunomodulatory agents, that is, they have dual mechanisms of action.

Alkylating Agents

Alkylating agents or DNA alkylating agents, as used herein, operate by damaging DNA. DNA damage could be accomplished by any one of the following mechanisms: In the first mechanism an alkylating agent attaches alkyl groups to DNA bases. This alteration results in the DNA being fragmented by repair enzymes in their attempts to replace the alkylated bases. A second mechanism by which alkylating agents cause DNA damage is the formation of cross-bridges, bonds between atoms in the DNA. In this process, two bases are linked together by an alkylating agent that has two DNA binding sites. Cross-linking prevents DNA from being separated for synthesis or transcription. The third mechanism of action of alkylating agents causes the mispairing of the nucleotides leading to mutations.

There are six groups of alkylating agents: nitrogen mustards; ethylenimes; alkylsulfonates; triazenes; piperazines; and nitrosureas. Examples of alkylating agents are, but limited to, thiotepa and cyclophosphamide (CYTOXAN™);

alkyl sulfonates such as busulfan, improsulfan and piposulfan; aziridines such as benzodopa, carboquone, carmustine, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8). The preferred alkylating agents are selected from melphalan and cyclophosphamide.

Corticosteroids

Corticosteroids are drugs closely related to cortisol, a hormone which is naturally produced in the adrenal cortex (the outer layer of the adrenal gland). Corticosteroid Drugs include: Betamethasone (Celestone), Budesonide (Entocort EC), Cortisone (Cortone), Dexamethasone (Decadron), Hydrocortisone (Cortef), Methylprednisolone (Medrol), Prednisolone (Prelone), Prednisone (Deltasone), and Triamcinolone (Kenacort, Kenalog). Preferred corticosteroid is Dexamethasone (including derivatives, such as but not limited to, dexamethasone sodium phosphate and dexamethasone acetate). Corticosteroids can be given orally, injected into the vein or muscle, applied locally to the skin, injected directly (for example, into inflamed joints). Corticosteroids can be used in conjunction with other drugs, and are prescribed for short-term and long-term use (e.g., given in pulse doses, doses administered for a short period of time, repeated at set intervals). Recommended dose of Corticosteroids may range from 0.5 to 100 mg/day. For example, For example, dexamethasone may be recommended at a range between 0.5 to 100 mg/day, more preferably between 10 to 80 mg/day, even more preferably at 15 to 70 mg/day or most preferably between 20 to 60 mg/day for administration on the same day or on different days, such as, on Days 1 to 4, 9 to 12, and 17 to 20 of each 28-day cycle for the first 4 cycles of therapy and then 40 mg/day orally on Days 1 to 4 every 28 days. Dosing can be continued or modified based upon clinical and laboratory findings. For example, the dose is initially quite high, then gradually tapered or vice a versa or that one may want to start you at a higher, or lower dose than what is recommended and may depend on the body weight of the mammalian (e.g., a human) being treated.

The drug conjugates may be prepared by biochemical methods. In order to link a drug or prodrug to the antibody, a linking group is used. Suitable linking groups are well known in the art and include disulfide groups, acid labile groups, photolabile groups, peptidase labile groups, thioether groups and esterase labile groups. Preferred linking groups are disulfide and thioether groups. For example, conjugates can be constructed using a disulfide exchange reaction between the appropriately modified antibody and the drug or prodrug, or by reaction of a thiol-containing drug with an antibody that has been modified to contain a maleimido group. Alternatively the drug may contain a maleimido group and the antibody a thiol moiety. Methods for the preparation of conjugates are described in the art (see U.S. Pat. Nos. 5,208,030; 5,416,064; 6,333,410; 6,441,163; 6,716,821; 6,913,748; 7,276,497 and US Application No. 2005/0169933. The drug molecules also can be linked to a cell-binding agent through an intermediary carrier molecule such as serum albumin.

In accordance with the invention, the cell-binding agent is modified by reacting a bifunctional crosslinking reagent with the cell-binding agent, thereby resulting in the covalent attachment of a linker molecule to the cell-binding agent. As used herein, a "bifunctional crosslinking reagent" is any chemical moiety that covalently links a cell-binding agent to a drug, such as the drugs described herein. In a preferred embodiment of the invention, a portion of the linking moiety is provided by the drug. In this respect, the drug comprises a linking moiety that is part of a larger linker molecule that is used to join the cell-binding agent to the drug. For example, to form the maytansinoid DM1 or DM4, the ester side chain at the C-3 position of maytansine is modified to have a free sulfhydryl group (SH), as described in U.S. Pat. Nos. 5,208, 020; 6,333,410; 7,276,497. This thiolated form of maytansine can react with a modified cell-binding agent to form a conjugate. Therefore, the final linker is assembled from two components, one of which is provided by the crosslinking reagent, while the other is provided by the side chain from DM1 or DM4.

Any suitable bifunctional crosslinking reagent can be used in connection with the invention, so long as the linker reagent provides for retention of the therapeutic, e.g., cytotoxicity, and targeting characteristics of the drug and the cell-binding agent, respectively. Preferably, the linker molecule joins the drug to the cell-binding agent through chemical bonds (as described above), such that the drug and the cell-binding agent are chemically coupled (e.g., covalently bonded) to each other. Preferably, the linking reagent is a cleavable linker. More preferably, the linker is cleaved under mild conditions, i.e., conditions within a cell under which the activity of the drug is not affected. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., Proc. Natl. Acad. Sci. USA, 79: 626-629 (1982), and Umemoto et al., Int. J. Cancer, 43: 677-684 (1989)).

Preferably the drug is linked to a cell-binding agent through a disulfide bond or a thioether bond. The linker molecule comprises a reactive chemical group that can react with the cell-binding agent. Preferred reactive chemical groups for reaction with the cell-binding agent are N-succinimidyl esters and N-sulfosuccinimidyl esters. Additionally the linker molecule comprises a reactive chemical group, preferably a dithiopyridyl group that can react with the drug to form a disulfide bond. Particularly preferred linker molecules include, for example, N-succinimidyl 3-(2-pyridyldithio)propionate (SPDP) (see, e.g., Carlsson et al., *Biochem. J*, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and other reactive cross-linkers which are described in U.S. Pat. No. 6,913,748, which is incorporated herein in its entirety by reference.

While cleavable linkers preferably are used in the inventive method, a non-cleavable linker also can be used to generate the above-described conjugate. A non-cleavable linker is any chemical moiety that is capable of linking a drug, such as a maytansinoid, a Vinca alkaloid, a dolastatin, an auristatin, or a cryptophycin, to a cell-binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the drug or the cell-binding agent remains active.

Suitable crosslinking reagents that form non-cleavable linkers between a drug and the cell-binding agent are well known in the art. Examples of non-cleavable linkers include linkers having an N-succinimidyl ester or N-sulfosuccinimidyl ester moiety for reaction with the cell-binding agent, as well as a maleimido- or haloacetyl-based moiety for reaction with the drug. Crosslinking reagents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(β-maleimidophenyl)-butyrate (SMPB), and N-(β-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula (IX):

$$HOOC-X_l-Y_n-Z_m-COOH \qquad (IX),$$

wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. patent application Ser. No. 10/960,602. Other linkers which can be used in the present invention include charged linkers or hydrophilic linkers and are described in U.S. patent application Ser. Nos. 12/433,604 and 12/433,668, respectively.

Alternatively, as disclosed in U.S. Pat. No. 6,441,163 B1, the drug can be first modified to introduce a reactive ester suitable to react with a cell-binding agent. Reaction of these maytansinoids containing an activated linker moiety with a cell-binding agent provides another method of producing a cleavable or non-cleavable cell-binding agent maytansinoid conjugate.

The immunoconjugates and chemotherapeutic agents of the present invention can be administered in vitro, in vivo and/or ex vivo to treat patients and/or to modulate the growth of selected cell populations including, for example, cancer of the lung, blood, plasma, breast, colon, prostate, kidney, pancreas, brain, bones, ovary, testes, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like. Preferably, the immunoconjugates and chemotherapeutic agents of the invention are administered in vitro, in vivo and/or ex vivo to treat cancer in a patient and/or to modulate the growth of cancer cells, including, for example, cancer of the blood, plasma, lung, breast, colon, prostate, kidney, pancreas, brain, bones, ovary, testes, and lymphatic organs; preferably the cancer cells are breast cancer cells, prostate cancer cells, ovarian cancer cells, colorectal cancer cells, multiple myeloma cells, ovarian cancer cells, neuroblastoma cells, neuroendocrine cancer cells, gastric cancer cells, squamous cancer cells, small-cell lung cancer cells, or testicular cancer cells or a combination thereof.

"Modulating the growth of selected cell populations" includes inhibiting the proliferation of selected multiple myeloma cell populations (e.g., MOLP-8 cells, OPM2 cells, H929 cells, and the like) from dividing to produce more cells; reducing the rate of increase in cell division as compared, for example, to untreated cells; killing selected cell populations; and/or preventing selected cell populations (such as cancer cells) from metastasizing. The growth of selected cell populations can be modulated in vitro, in vivo or ex vivo.

In the methods of the present invention, the immunoconjugates and chemotherapeutic agents can be administered in vitro, in vivo, or ex vivo separately or as components of the same composition. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect. The anti-cancer drugs that can be administered include a DNA alkylating agent, such as, melphalan; a proteasome inhibitor, such as, bortezomib (Velcade); and immunomodulatory or anti-angiogenic agents, such as, thalidomide and lenalidomide (Revlimid), along with the corticosteroid dexamethasone. Thus, for example, the antibody-maytansinoid conjugate can be combined with just one of the chemotherapeutic agents listed above or a combination two or more chemotherapeutic agents listed above. For example, the antibody-maytansinoid conjugate can be combined with bortezomib and lenalidomide or thalidomide with or without added dexamethasone. Similarly the antibody-maytansinoid conjugate can be combined with melphalan and bortezomib or lenalidomide, with or without added dexamethasone. The order of administration and doses for each agent are readily determined by one skilled in the art using the approved schedule of administration for the individual agents (see for example Physicians Desk Reference, (PDR) 2006 discloses the preferred doses of treatment and dosing schedules for thalidomide (p 979-983) Velcade (p 2102-2106) and melphalan (p 976-979).

The immunoconjugates and chemotherapeutic agents can be used with suitable pharmaceutically acceptable carriers, diluents, and/or excipients, which are well known, and can be determined, by one of skill in the art as the clinical situation warrants. Examples of suitable carriers, diluents and/or excipients include: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The compounds and compositions described herein may be administered in appropriate form, preferably parenterally, more preferably intravenously. For parenteral administration, the compounds or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

The compositions can also be in the form of sterile solid compositions which can be dissolved or dispersed in sterile water or any other injectable sterile medium.

The "therapeutically effective amount" of the chemotherapeutic agents and immunoconjugates described herein refers to the dosage regimen for inhibiting the proliferation of selected cell populations and/or treating a patient's disease, and is selected in accordance with a variety of factors, including the age, weight, sex, diet and medical condition of the patient, the severity of the disease, the route of administration, and pharmacological considerations, such as the activity, efficacy, pharmacokinetic and toxicology profiles of the particular compound used. The "therapeutically effective amount" can also be determined by reference to standard medical texts, such as the Physicians Desk Reference 2004. The patient is preferably an animal, more preferably a mammal, most preferably a human. The patient can be male or female, and can be an infant, child or adult.

Examples of suitable protocols of immunoconjugate administration are as follows. Immunoconjugates can be given daily for about 5 days either as an i.v. bolus each day for about 5 days, or as a continuous infusion for about 5 days.

Alternatively, they can be administered once a week for six weeks or longer. As another alternative, they can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period. Dosages will be about 10 pg to about 1000 mg/kg per person, i.v. (range of about 100 ng to about 10 mg/kg).

About one to about four weeks after treatment, the patient can receive a second course of treatment. Specific clinical protocols with regard to route of administration, excipients, diluents, dosages, and times can be determined by the skilled artisan as the clinical situation warrants.

The present invention also provides pharmaceutical kits comprising one or more containers filled with one or more of the ingredients of the pharmaceutical compounds and/or compositions of the present invention, including, one or more immunoconjugates and one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. The 2006 edition of the Physician's Desk Reference (PDR) discloses the mechanism of action and preferred doses of treatment and dosing schedules for thalidomide (p 979-983) Velcade (p 2102-2106) and melphalan (p 976-979). The contents of the PDR are expressly incorporated herein in their entirety by reference. One of skill in the art can review the PDR, using one or more of the following parameters, to determine dosing regimen and dosages of the chemotherapeutic agents and conjugates that can be used in accordance with the teachings of this invention. These parameters include:

1. Comprehensive index
   a) by Manufacturer
   b) Products (by company's or trademarked drug name)
   c) Category index (for example, "proteasome inhibitors", "DNA alkylating agents," "melphalan" etc.)
   d) Generic/chemical index (non-trademark common drug names)
2. Color images of medications
3. Product information, consistent with FDA labeling
   a) Chemical information
   b) Function/action
   c) Indications & Contraindications
   d) Trial research, side effects, warnings Analogues and Derivatives One skilled in the art of therapeutic agents, such as cytotoxic agents or chemotherapeutic agents, will readily understand that each of the such agents described herein can be modified in such a manner that the resulting compound still retains the specificity and/or activity of the starting compound. The skilled artisan will also understand that many of these compounds can be used in place of the therapeutic agents described herein. Thus, the therapeutic agents of the present invention include analogues and derivatives of the compounds described herein.

All references cited herein and in the examples that follow are expressly incorporated by reference in their entireties.

EXAMPLES

The invention will now be described by reference to non-limiting examples. Unless otherwise specified, all percents and ratios are by volume.

Mice were inoculated with human multiple myeloma tumor cell lines and allowed to become established (average tumor size of about 100 mm$^3$) prior to treatment. Conjugate dosing is described based on DM1 concentration. Efficacy is reported as both the % of tumor growth for treated vs. control (% T/C) and log cell kill (LCK) determined from the tumor doubling time and the tumor growth delay due to the treatment. Percent T/C values less than 42% and/or LCK values of 0.5 or greater are considered active; percent T/C values less than 10% are considered highly active (Bissery et al., Cancer Res, 51: 4845-4852 (1991).

Example 1

Anti-Tumor Effect of Combination Therapy of Human Multiple Myeloma (MOLP-8) Xenografts with huN901-DM1 and Melphalan The anti-tumor effect of a combination of huN901-DM1 and melphalan was evaluated in an established subcutaneous xenograft model of multiple myeloma. Balb/c nude mice (20 animals) were inoculated with MOLP-8 human multiple myeloma cells ($1 \times 10^7$ cells/animal) injected subcutaneously into the right shoulder of the mice. When the tumors reached about 150 mm$^3$ in size (21 days after tumor cell inoculation), the mice were randomly divided into four groups (5 animals per group). The first group of mice was treated with huN901-

DM1 (DM1 dose of 200 µg/kg single injection, day 22 post tumor cell inoculation) administered intravenously. A second group of animals was treated with melphalan (12 mg/kg, single injection, day 23 post tumor cell inoculation) administered intraperitoneally. The third group of mice received a combination of huN901-DM1 and melphalan using the same doses, schedules and routes of administration as in groups 1 and 2. A control group of animals received phosphate-buffered saline (PBS) using the same schedules and routes of administration as in groups 1 and 2. Tumor growth was monitored by measuring tumor size twice per week. Tumor size was calculated with the formula: length×width×height×½.

Tumor growth data are shown in FIG. 1A. In the control group of animals, tumors grew to 1000 mm$^3$ in approximately 33 days. Treatment with huN901-DM1 or melphalan alone resulted in tumor growth delays of 11 days and 14 days respectively. In contrast, treatment with the combination of melphalan and huN901-DM1 resulted in a tumor growth delay of 35 days, and was highly active according to NCI standards (T/C=4%, see Table 1 (FIG. 1B)).

The combination treatment log cell kill (LCK) was 2.1, which is greater than the sum of LCK values for the individual drugs, indicating synergistic activity.

Example 2

Anti-Tumor Effect of Combination Therapy of Human Multiple Myeloma (MOLP-8) Xenografts with huN901-DM1 and Thalidomide The anti-tumor effect of a combination of huN901-DM1 and thalidomide was evaluated in an established subcutaneous xenograft model of multiple myeloma. SCID mice (36 animals) were inoculated with MOLP-8 human multiple myeloma cells (1×10$^7$ cells/animal) injected subcutaneously into the right shoulder of the mice. When the tumors reached about 150 mm$^3$ in size (15 days after tumor cell inoculation), the mice were randomly divided into six groups (6 animals per group). Two groups of mice were treated with the single agent huN901-DM1 at DM1 doses of 100 µg/kg and 250 µg/kg, respectively (1qw×2, days 16 and 23 post tumor cell inoculation) administered intravenously. A third group of mice was treated with the single agent thalidomide at a dose of 200 mg/kg (11 doses total on days 16, 18-22, and 25-29 post tumor cell inoculation), administered intraperitoneally as a suspension in 1% carboxymethylcellulose in PBS. Two groups were treated with combinations of huN901-DM1 (100 µg/kg or 250 µg/kg) plus thalidomide using the same doses, schedules and administration routes used for single agent treated groups. A control group of animals received PBS administered intravenously (1qw×2, days 16 and 23 post tumor cell inoculation). Tumor growth was monitored by measuring tumor size twice per week. Tumor size was calculated with the formula: length×width×height×½.

Figure 2A:
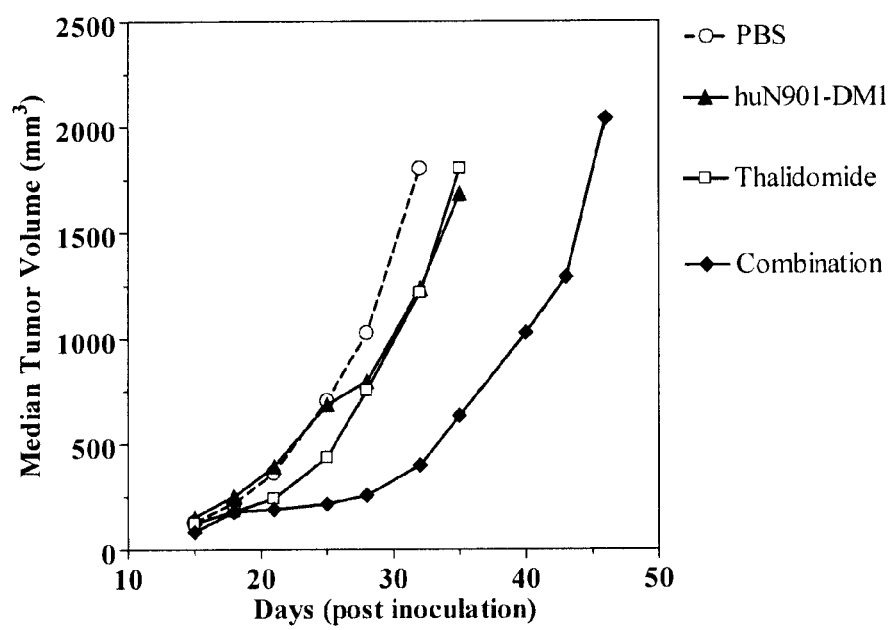
Figure 2B:
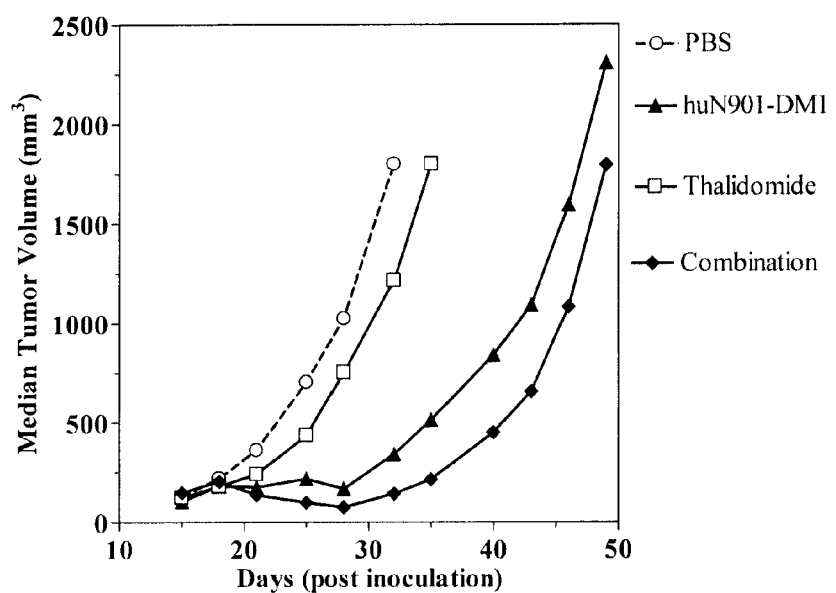

Tumor growth data are shown in FIGS. 2A and 2B. The combination of huN901-DM1 plus thalidomide was active in MOLP-8 xenografts, resulting in additive to synergistic activity (Table 2 (FIG. 2C)). The combination of huN901-DM1 and thalidomide at doses that were inactive as single agents (100 µg/kg huN901-DM1, 200 mg/kg thalidomide) was active according to NCI standards (T/C=26%; Table 2 (FIG. 2C)).

The combination of huN901-DM1 (250 µg/kg) plus thalidomide (200 mg/kg) resulted in a highly active combination (T/C=7%) with log cell kill of 1.0 which is greater than the sum of LCK values for the individual drugs.

Example 3

Anti-Tumor Effect of Combination Therapy of Human Multiple Myeloma (OPM2) Xenografts with huN901-DM1 and Bortezomib The anti-tumor effect of a combination of huN901-DM1 and bortezomib (Velcade, Millennium Pharmaceuticals) was evaluated in an established subcutaneous xenograft model of multiple myeloma. SCID mice (36 animals) were inoculated with OPM2 human multiple myeloma cells (1×10$^7$ cells/animal) injected subcutaneously into the right shoulder of the mice. When the tumors reached about 70 mm$^3$ in size (12 days after tumor cell inoculation), the mice were randomly divided into six groups (6 animals per group). Two groups of mice were treated with the single agent huN901-DM1 at DM1 doses of 100 µg/kg and 200 µg/kg, respectively (day 12 post tumor cell inoculation) administered intravenously. A third group of mice was treated with the single agent bortezomib at a dose of 1 mg/kg (days 13 and 16 post tumor cell inoculation), administered intravenously. Two groups were treated with combinations of huN901-DM1 (100 µg/kg or 200 µg/kg) plus bortezomib using the same doses, schedules and administration routes used for single agent treated groups. A control group of animals received PBS administered intravenously (day 12 post tumor cell inoculation). Tumor growth was monitored by measuring tumor size twice per week. Tumor size was calculated with the formula: length×width×height×½.

Figure 3A:
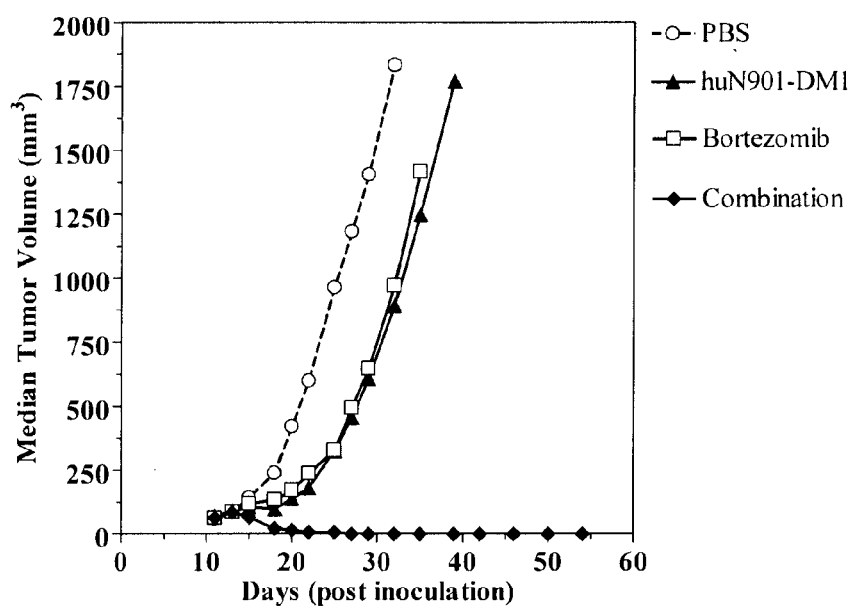
Figure 3B:
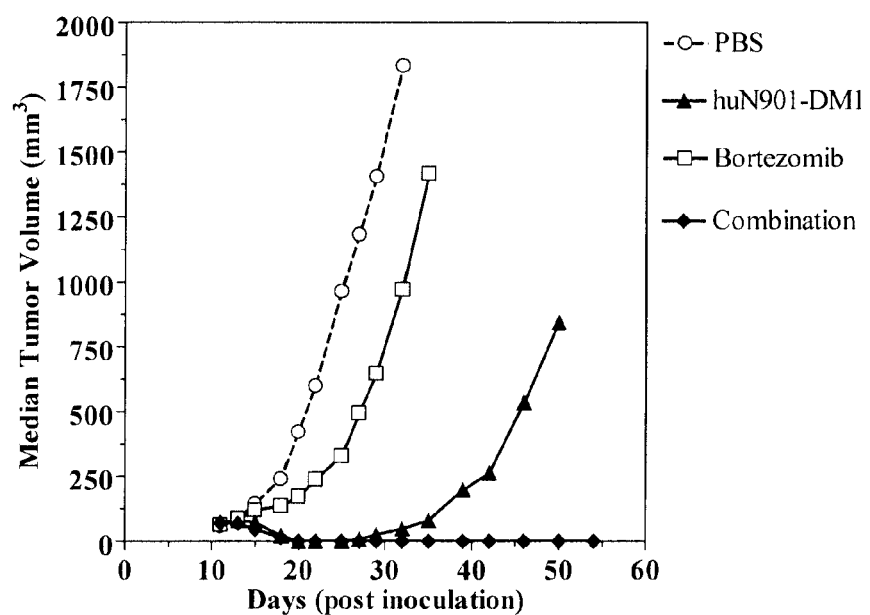

The combination of huN901-DM1 plus bortezomib was highly active in OPM2 xenografts, resulting in synergistic activity with both dose combinations. Treatment with huN901-DM1 alone resulted in 1 of 6 and 3 of 6 tumor-free mice at day 91, for the 100 and 200 µg/kg doses, respectively (see Table 3 (FIG. 3C)). There were no tumor-free mice at this time in the bortezomib single agent group. Both combinations of huN901-DM1 plus bortezomib (1 mg/kg) resulted in complete tumor regressions in 6 of 6 mice, with mice remaining tumor-free to day 91, the date of the last tumor measurements. Tumor growth curves are shown in FIGS. 3A and 3B.

The combination of huN901-DM1 plus bortezomib resulted in a highly active combination that was synergistic.

Example 4

Anti-Tumor Effect of Combination Therapy of Human Multiple Myeloma (H929) Large Tumor Xenografts with huN901-DM1 and Bortezomib The anti-tumor effect of a combination of huN901-DM1 and bortezomib was evaluated in an established subcutaneous xenograft model of multiple myeloma. SCID mice (54 animals) were inoculated with H929 human multiple myeloma cells (1×10$^7$ cells/animal) injected subcutaneously into the right shoulder of the mice. When the tumors reached about 300 mm$^3$ in size (34 days after tumor cell inoculation), the mice were randomly divided into 11 groups (6 animals per group). Two groups of mice were treated with the single agent huN901-DM1 at DM1 doses of 50 µg/kg and 100 µg/kg, respectively (day 34 post tumor cell inoculation) administered intravenously. Two groups of mice were treated with the single agent bortezomib at a 0.5 mg/kg low dose and 1 mg/kg high dose (days 35 and 38 post tumor cell inoculation) administered intravenously. Four combination groups were evaluated, with combinations of each dose of huN901-DM1 plus low- or high-dose bortezomib using the same schedules used for single agent treated groups. A control group of animals received PBS administered intravenously (day 34 post tumor cell inoculation). Tumor growth was monitored by measuring tumor size twice per week. Tumor size was calculated with the formula: length×width×height×½.

Figure 4A:
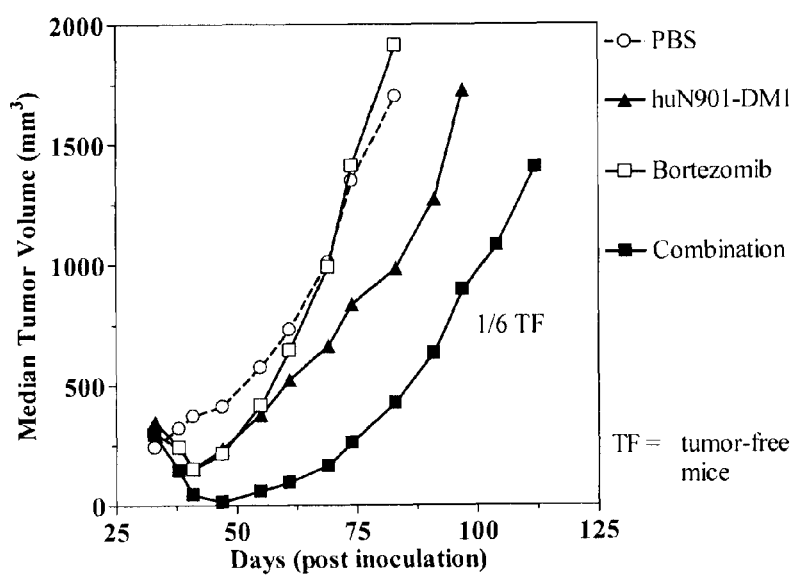
FIG. 4A shows a combination of huN901-DM1 with bortezomib (low-dose) in large H929 multiple myeloma xenografts.

Combination of huN901-DM1 with low-dose bortezomib in H929 tumors was synergistic. The combination of huN901-DM1 and bortezomib at doses that were inactive as single agents (50 µg/kg huN901-DM1, 0.5 mg/kg bortezomib) was active according to NCI standards (T/C=38%; see Table 4a (FIG. 4B)). Combination of huN901-DM1 (100 µg/kg) plus bortezomib at 0.5 mg/kg also resulted in an active combination (T/C=17%, 1 of 6 mice tumor-free at the end of the study on day 119; see FIG. 4A).

Figure 4C:
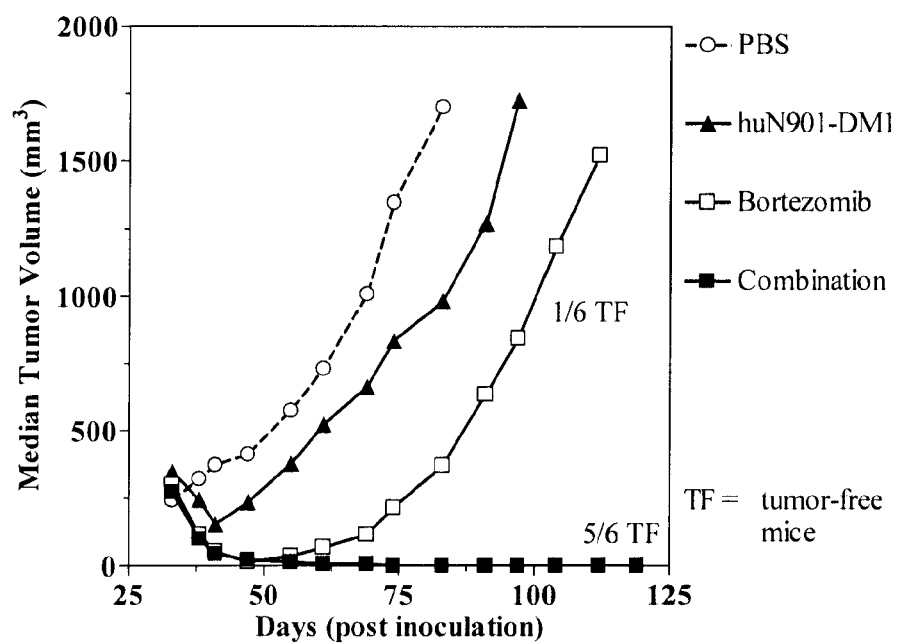
FIG. 4C shows a combination of huN901-DM1 with bortezomib (high-dose) in large H929 multiple myeloma xenografts.

Combination of huN901-DM1 with high-dose bortezomib in H929 tumors was also synergistic. The high-dose bortezomib (1.0 mg/kg), is active as a single agent in the H929 large tumor model (T/C=11%, 1 of 6 mice tumor-free at day 119; see Table 4b (FIG. 4D)). The combination treatments of high-dose bortezomib with huN901-DM1 at 50 and 100 µg/kg were highly active, as indicated by the low T/C values of 7% and 0%, respectively; with the latter combination resulting in 5/6 tumor-free mice at day 119 (see FIG. 4C). The combination of huN901-DM1 plus bortezomib resulted in a highly active combination that was synergistic.

Example 5

Anti-Tumor Effect of Combination Therapy of Human Multiple Myeloma (OPM2) Xenografts with huN901-DM1 and Lenalidomide The anti-tumor effect of a combination of huN901-DM1 and lenalidomide was evaluated in an established subcutaneous xenograft model of multiple myeloma. SCID mice (20 animals) were inoculated with OPM2 human multiple myeloma cells ($1 \times 10^7$ cells/animal) injected subcutaneously into the right shoulder of the mice. When the tumors reached about 130 mm³ in size (16 days after tumor cell inoculation), the mice were randomly divided into four groups (5 animals per group). One group of mice was treated with the single agent huN901-DM1 (200 µg/kg, day 16 post tumor cell inoculation) administered intravenously. A second group of mice was treated with the single agent lenalidomide at (100 mg/kg, days 16-20, 22-26 post tumor cell inoculation), administered as a suspension in 1% carboxymethylcellulose/PBS by intraperitoneal injection. A third group was treated with a combination of huN901-DM1 plus lenalidomide using the same doses, schedules and administration routes used for single agent treated groups. A control group of animals received PBS administered intravenously (day 16 post tumor cell inoculation). Tumor growth was monitored by measuring tumor size twice per week. Tumor size was calculated with the formula: length×width×height×½.

Figure 5A:
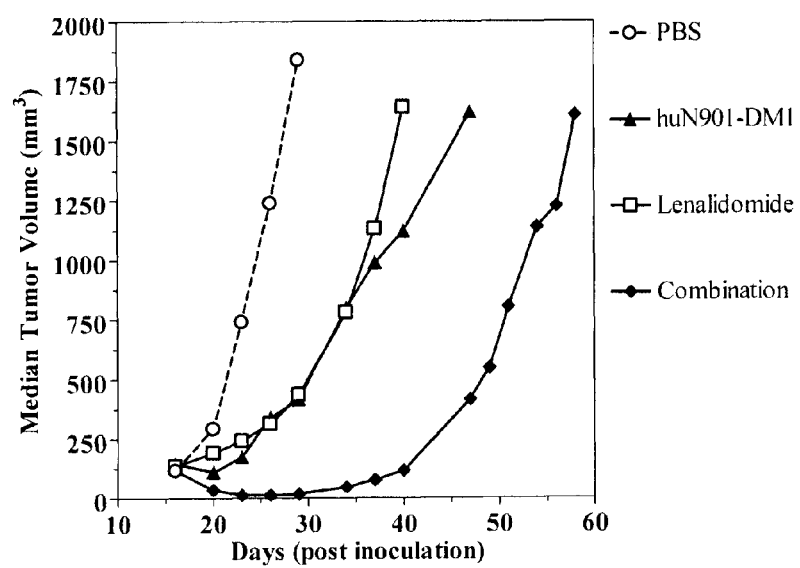
FIG. 5A shows a combination of huN901-DM1 with lenalidomide in OPM2 multiple myeloma xenografts.

Treatment with a single injection of huN901-DM1 (200 µg/kg, day 16) was active against OPM2 multiple myeloma xenografts (T/C=26%, LCK=0.9; see Table 5 (FIG. 5B)); the activity of lenalidomide as a single agent (100 mg/kg, days 16-20, 23-27) was comparable (T/C=28%, LCK=0.9). The combination of huN901-DM1 plus lenalidomide was highly active (T/C=1.4%, LCK=1.7) with 1/5 mice tumor-free at the end of the study; there were no tumor-free survivors in the either the huN901-DM1 or lenalidomide/dexamethasone treatment groups. The results of this study show that combination treatment is synergistic, showing greater activity than the drugs as single agents. Tumor growth data are shown in Table 5 (FIG. 5B) and FIG. 5A).

Example 6

Schedule Dependency of the Anti-Tumor Effect of the Combination of huN901-DM1 with Bortezomib The anti-tumor effect of a combination of huN901-DM1 and bortezomib (Velcade, Millennium Pharmaceuticals) was evaluated in an established subcutaneous xenograft model of multiple myeloma. The objective of this study was to determine the optimal schedule for the combination therapy. SCID mice (18 animals) were inoculated with OPM2 human multiple myeloma cells ($1 \times 10^7$ cells/animal) injected subcutaneously into the right shoulder of the mice. When the tumors reached about 70 mm³ in size (12 days after tumor cell inoculation), the mice were randomly divided into three groups (6 animals per group). The first group of mice was treated first with bortezomib at a dose of 1 mg/kg on days 0 and 3, followed by huN901-DM1 at a dose of 13 mg/kg on day 3. In the alternative schedule, the second group of mice was treated first with huN901-DM1 at a dose of 13 mg/kg on day 0, followed 3 days later (days 3 and 6) with bortezomib at a dose of 1 mg/kg. A control group of animals received PBS administered intravenously (day 12 post tumor cell inoculation). Tumor growth was monitored by measuring tumor size twice per week. Tumor size was calculated with the formula: length×width×height×½.

Figure 6:
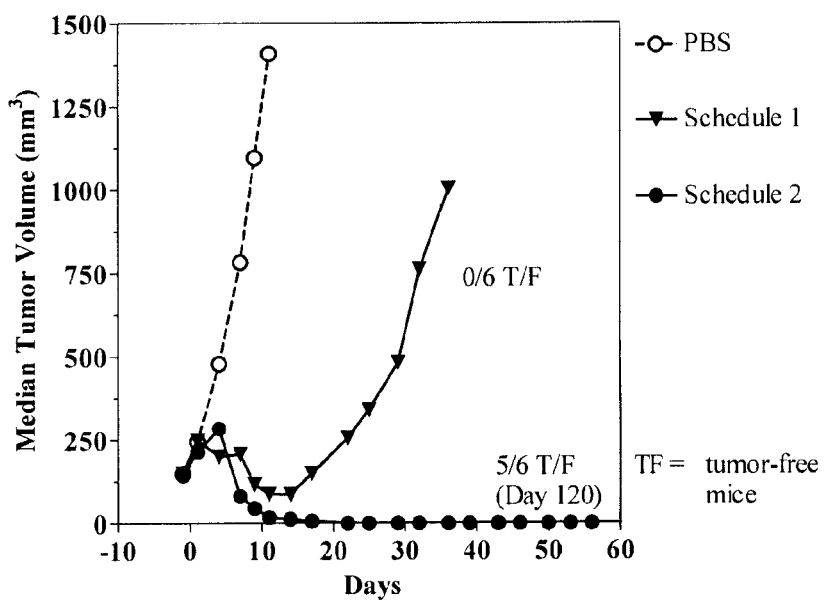
FIG. 6 shows a schedule dependency of the anti-tumor activity of huN901-DM1 with bortezomib. Schedule 1: huN901-DM1 day 0; bortezomab: day 3,6. Schedule 2: bortezomib day 0.3; huN901-DM1 day 3).

Unexpectedly, the combination of huN901-DM1 plus bortezomib was highly active in OPM2 xenografts, only when bortezomib was administered first (see FIG. 6). Thus, this schedule resulted in complete regression of the tumors, with 5 out of 6 mice being tumor free on day 120. When bortezomib was administered second (i.e. after huN901-DM1 administration), the treatment only resulted in a modest delay in tumor growth, with no animals being tumor-free even on day 30. This data suggests that in combination therapy with bortezomib and immunoconjugate, the schedule of administration is critical. It is conceivable that pre-treatment with bortezomib might sensitize tumor cells to killing by the immunoconjugate huN901-DM1.

Example 7

Anti-Tumor Effect of Triple-Combination Therapy of Human Multiple Myeloma (MOLP-8) Xenografts with huN901-DM1 and Lenalidomide Plus Low-Dose Dexamethasone The anti-tumor effect of a triple-combination of huN901-DM1 and lenalidomide plus low-dose dexamethasone was evaluated in an established subcutaneous xenograft model of multiple myeloma. SCID mice were inoculated with MOLP-8 human multiple myeloma cells ($1.5 \times 10^7$ cells/animal) injected subcutaneously into the right shoulder of the mice. When the tumors reached about 100 mm³ in size (13 days after tumor cell inoculation), 24 mice were randomly divided into four groups (6 animals per group). Treatments were initiated on day 13 post inoculation, indicated as day 1 of treatment. One group of mice was treated with the single agent huN901-DM1 (150 µg/kg, administered intravenously on days 1 and 8). A second group of mice was treated with the combination of lenalidomide/low-dose dexamethasone (lenalidomide at 100 mg/kg, administered as a suspension in 1% carboxymethylcellulose/PBS by intraperitoneal injection on days 1-5, 8-12; dexamethasone at 1.5 mg/kg, administered by subcutaneous injection on days 1 and 8). A third group was treated with the triple-combination of huN901-DM1 plus lenalidomide/dexamethasone using the same doses, schedules and administration routes used for individual treatment groups. A control group of animals received PBS administered intravenously (days 1 and 8). Tumor growth was monitored by measuring tumor size twice per week. Tumor size was calculated with the formula: length×width×height×½.

Figure 7A:
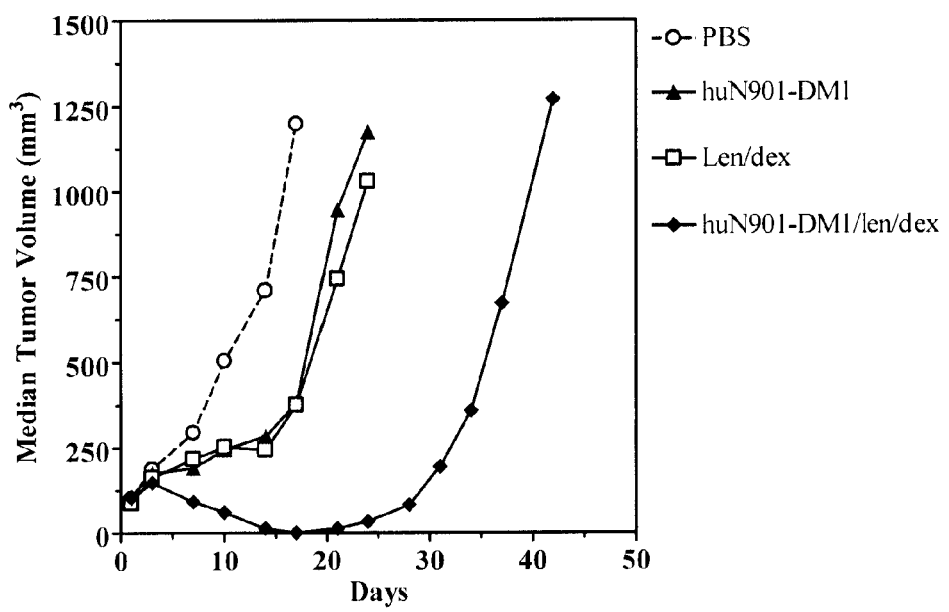
FIG. 7A shows a triple combination of huN901-DM1 with lenalidomide plus low-dose dexamethasone in MOLP-8 multiple myeloma xenografts. Lenalidomide (100 mg/kg, qd×5× 2) was administered at days 1-5 and 8-12. Dexamethasone (1.5 mg/kg, qw×2) was administered at days 1 and 8, as was huN901-DM1 (150 μg/kg, qw×2).

Treatments with huN901-DM1 (150 ng/kg, qw×2) or lenalidomide plus dexamethasone were equally active against MOLP-8 tumors (T/C=33%, LCK=0.5; see Table 7 (FIG. 7B)). The triple-combination of huN901-DM1/lenalidomide/dexamethasone was highly active (T/C=0%, LCK=1.4) with all of the mice (6/6) experiencing partial regressions and 4/6 mice with complete tumor regressions, compared with no regressions in either the huN901-DM1 or lenalidomide/dexamethasone treatment groups. Tumor growth data are shown in Table 7 (FIG. 7B) and FIG. 7A.

Figure 8A:
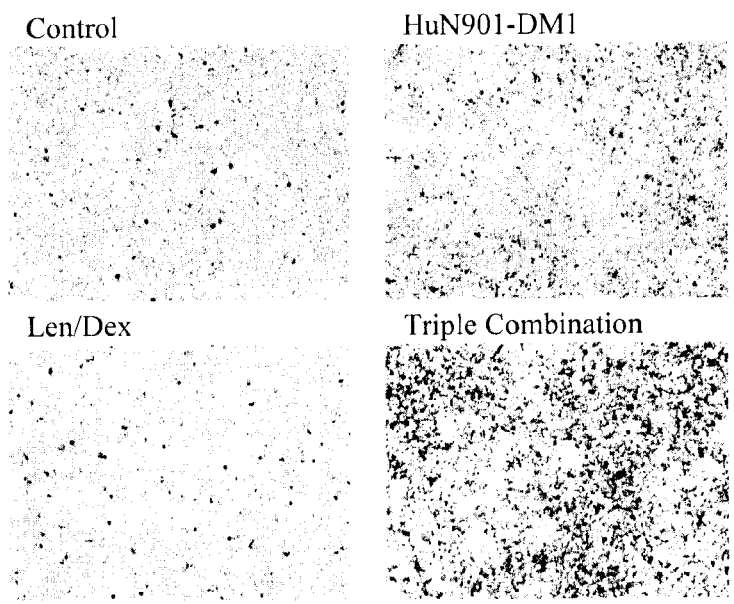
FIG. 8A shows immunohistochemical analysis of the apoptosis marker, caspase-3 in MOLP-8 multiple myeloma xenografts following treatment with the triple combination of huN901-DM1 with lenalidomide plus low-dose dexamethasone. Immunohistochemical staining of MOLP-8 xenographs collected 48 hours post treatment was performed with an antibody to cleaved-caspase 3.
Figure 8B:
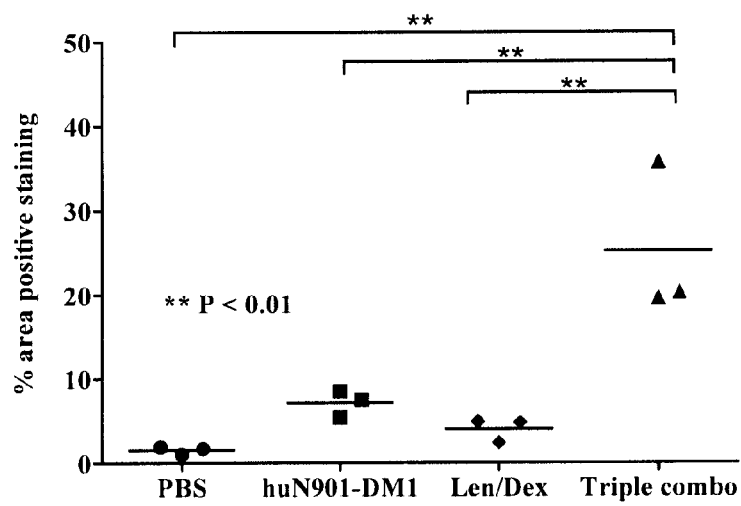
FIG. 8B shows the statistically significant synergistic increase in tumor cell apoptosis in MOLP-8 multiple myeloma xenografts treated with the triple combination of huN901-DM1 with lenalidomide plus low-dose dexamethasone compared to treatment with either therapy separately. Percent area positive staining for cleaced-caspase-3 was determined using ImageJ image analysis software, with one-way ANOVA statistical analysis using GraphPad Prism.

Satellite treatment groups of MOLP-8 tumor-bearing mice (3 animals per group) were treated in parallel to the efficacy study, sacrificed on day 3 (after 48 hours of treatment) and tumors were collected for immunohistochemical with an antibody to cleaved caspase-3, to assess apoptosis. Tumors from mice treated with the triple combination of huN901-DM1/lenalidomide/dexamethasone exhibited significant increase in caspase-3 staining relative to the control and single-therapy treatment groups had apoptosis levels at or near baseline (data are shown in FIG. 8A). This sharp increase in apoptosis with the triple-combination is evident early in the treatment phase, before any changes in tumor volume were detected in the anti-tumor activity study.

The results of these studies show that the triple combination treatment with huN901-DM1/lenalidomide/dexamethasone is synergistic, showing greater anti-tumor activity and a significant increase in tumor cell apoptosis than the agents as separate therapies.

The invention claimed is:

1. A method for treating or modulating the growth of multiple myeloma cells comprising administering to a subject with multiple myeloma, a synergistically effective amount of lenalidomide, dexamethasone, and at least one immunoconjugate, wherein the immunoconjugate comprises at least one cell-binding agent that specifically binds to CD56 antigen expressed on said multiple myeloma cells and a maytansinoid covalently conjugated to said cell-binding agent, wherein the cell-binding agent is an antibody, a single chain antibody or an antigen-binding antibody fragment.

2. The method of claim 1, wherein the lenalidomide, dexamethasone, and at least one immunoconjugate are administered simultaneously, sequentially, or separately.

3. The method of claim 2, wherein the lenalidomide, dexamethasone, and at least one immunoconjugate are administered every other day, on alternate days, on a weekly basis or time period between day 0 and 7, or between 0 and 4 weeks.

4. The method of claim 1, wherein the lenalidomide, dexamethasone, and at least one immunoconjugate are administered parenterally.

5. The method of claim 1, wherein the cell-binding agent is a monoclonal antibody, a single chain monoclonal antibody, or a monoclonal antigen-binding anti body fragment.

6. The method of claim 1, wherein the cell-binding agent is a chimeric antibody or a chimeric antigen-binding antibody fragment.

7. The method of claim 1, wherein the cell-binding agent is a domain antibody or a domain antigen-binding antibody fragment.

8. The method of claim 1, wherein the cell-binding agent is a resurfaced antibody, a resurfaced single chain antibody, or a resurfaced antigen-binding antibody fragment.

9. The method of claim 1, wherein the cell-binding agent is a humanized antibody, a humanized single chain antibody, or a humanized antigen-binding antibody fragment.

10. The method of claim 1, wherein the cell-binding agent is a human antibody, a human single chain antibody, or a human antigen-binding antibody fragment.

11. The method of claim 1, wherein the cell-binding agent is an N901 antibody, a single chain N901 antibody, or an antigen-binding N901 antibody fragment.

12. The method of claim 2, wherein the cell-binding agent is humanized or resurfaced N901, a single chain humanized or resurfaced N901 antibody or a humanized or resurfaced antigen-binding N901 antibody fragment.

13. The method of claim 1, wherein the maytansinoid has an N-methyl-alanine-containing C-3 thiol moiety.

14. The method of claim 13, wherein the maytansinoid is a compound of formula:

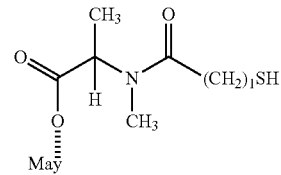

wherein l is an integer of from 1 to 10; and May is a maytansinoid.

15. The method of claim 13, wherein the maytansinoid is a compound of formula:

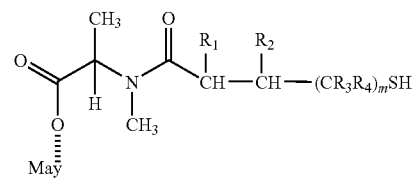

wherein $R_1$, $R_2$, $R_3$, $R_4$ are H, $CH_3$ or $CH_2CH_3$, and may be the same or different; m is 0, 1, 2 or 3; and May is a maytansinoid.

16. The method of claim 15, wherein $R_1$, $R_2$, $R_3$, $R_4$ are H, and m is 0.

17. The method of claim 13, wherein the maytansinoid is a compound of formula:

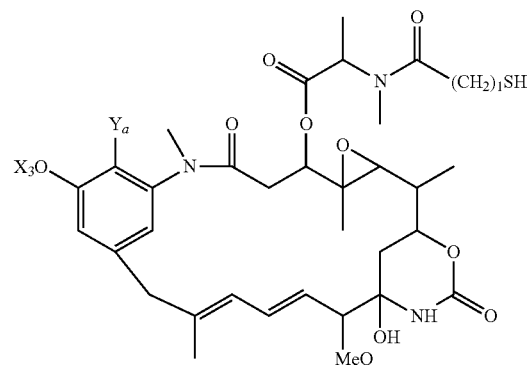

wherein l is 1, 2 or 3; $Y_0$ is Cl or H; and $X_3$ is H or $CH_3$.

18. A method for treating multiple myeloma comprising administering to a subject in need thereof a combination comprising a synergistically effective amount of lenalidomide, dexamethasone, and at least one immunoconjugate, and a pharmaceutically acceptable carrier for each;
    wherein the immunoconjugate comprises at least one cell-binding agent that specifically binds to CD56 antigen expressed on multiple myeloma cells and a maytansinoid covalently conjugated to said cell-binding agent; and
    wherein the cell-binding agent is an antibody, a single chain antibody or an antigen-binding antibody fragment.

19. A method for treating or modulating the growth of multiple myeloma cells comprising administering to a subject in need thereof, a combination comprising a synergistically effective amount of (i) lenalidomide, (ii) dexamethasone, and (iii) an immunoconjugate comprising a maytansinoid covalently conjugated to a humanized or resurfaced monoclonal antibody or fragment thereof that binds specifically to a CD56 antigen expressed by multiple myeloma cancer cells; and a pharmaceutically acceptable carrier for each.

20. The method of claim 1, wherein the immunoconjugate comprises maytansinoid drug DM1 covalently linked to a humanized or resurfaced N901 antibody.

21. The method of claim 17, wherein l=2.

22. The method of claim 1, wherein the maytansinoid is linked to the cell-binding agent through a linker molecule selected from the group consisting of N-succinimidyl 3-(2-pyridyldithio)propionate (SPDP), N-succinimidyl 4-(2-pyridyldithio)butanoate (SPDB) and N-succinimidyl 4-(2-pyridyldithio)pentanoate (SPP).

23. The method of claim 22, wherein the linker molecule is N-succinimidyl 4-(2-pyridyldithio)pentanoate (SPP).

24. The method of claim 20, wherein the DM1 and antibody are linked with N-succinimidyl 4-(2-pyridyldithio)pentanoate (SPP) linker molecule.

25. The method of claim 1, wherein the cell-binding agent is humanized or resurfaced N901 antibody, the maytansinoid is DM1, and the cell-binding agent is linked to the maytansinoid through a N-succinimidyl 4-(2-pyridyidithio)pentanoate (SPP) linker molecule.

26. The method of claim 18, wherein the cell-binding agent is humanized or resurfaced N901 antibody, single chain humanized or resurfaced N901 antibody or humanized or resurfaced antigen-binding N901 antibody fragment.

27. The method of claim 18, wherein the immunoconjugate comprises maytansinoid drug DM1 covalently linked to a humanized or resurfaced N901 antibody.

28. The method of claim 18, wherein the maytansinoid is linked, to the cell-binding agent through a linker molecule selected from the group consisting of N-succinimidyl 3-(2-pyridyldithio)propionate (SPDP), N-succinimidyl 4-(2-pyridyldithio)butanoate (SPDB) and N-succinimidyl 4-(2-pyridyldithio)pentanoate (SPP).

29. The method of claim 28, wherein the linker molecule is N-succinimidyl 4-(2-pyridyldithio)pentanoate (SPP).

30. The method of claim 27, wherein the DM1 and antibody are linked with N-succinimidyl 4-(2-pyridyldithio)pentanoate (SPP) linker molecule.

31. The method of claim 19, wherein the immunoconjugate comprises maytansinoid drug DM1 covalently linked to a humanized or resurfaced N901 antibody.

32. The method of claim 19, wherein the maytansinoid is linked to the cell-binding agent through a linker molecule selected from the group consisting of N-succinimidyl 3-(2-pyridyldithio)propionate (SPDP), N-succinimidyl 4-(2-pyridyldithio)butanoate (SPDB) and N-succinimidyl 4-(2-pyridyldithio)pentanoate (SPP).

33. The method of claim 32, wherein the linker molecule is N-succinimidyl 4-(2-pyridyldithio)pentanoate (SPP).

34. The method of claim 31, wherein the DM1 and antibody are linked with N-succinimidyl 4-(2-pyridyldithio)pentanoate (SPP) linker molecule.

35. A method for modulating the growth of multiple myeloma cells comprising contacting the multiple myeloma cells with a synergistically effective amount of lenalidomide, dexamethasone, and at least one immunoconjugate, wherein the immunoconjugate comprises at least one cell-binding agent that specifically binds to CD56 antigen expressed on said multiple myeloma cells and a maytansinoid covalently conjugated to said cell-binding agent;
    wherein the cell-binding agent is an antibody, a single chain antibody or an antigen-binding antibody fragment.

36. The method of claim 35, wherein the cell-binding agent is an N901 antibody, a single chain N901 antibody or an antigen-binding N901 antibody fragment.

37. The method of claim 35, wherein the cell-binding agent is a humanized or resurfaced N901 antibody, a single chain humanized N901 antibody or a humanized or resurfaced antigen-binding N901 antibody fragment.

38. The method of claim 35, wherein the immunoconjugate comprises maytansinoid drug DM1 covalently linked to a humanized or resurfaced N901 antibody.

39. The method of claim 35, wherein the maytansinoid is linked to the cell-binding agent through a linker molecule selected from the group consisting of N-succinimidyl 3-(2-pyridyldithio)propionate (SPDP), N-succinimidyl 4-(2-pyridyldithio)butanoate (SPDB) and N-succinimidyl 4-(2-pyridyldithio)pentanoate (SPP).

40. The method of claim 39, wherein the linker molecule is N-succinimidyl 4-(2-pyridyldithio)pentanoate (SPP).

41. The method of claim 2, wherein the lenalidomide, dexamethasone, and at least one immunoconjugate are administered once every two weeks, once every three weeks, or once every four weeks.

42. The method of claim 1, wherein the maytansinoid is DM1.

43. The method of claim 18, wherein the maytansinoid is DM1.

44. The method of claim 19, wherein the maytansinoid is DM1.

45. The method of claim 35, wherein the maytansinoid is DM1.

* * * * *